United States Patent
Reddy et al.

(10) Patent No.: US 8,945,468 B2
(45) Date of Patent: Feb. 3, 2015

(54) APPARATUS AND METHOD FOR STERILIZING ITEMS

(75) Inventors: Ganta S. Reddy, Cincinnati, OH (US); Ramgopal Vissa, Hyderbad (IN); Jaingesh A. Sekhar, Cincinnati, OH (US)

(73) Assignee: Micropyretics Heaters International, Inc., Cincinnati, OH (US)

( * ) Notice: Subject to any disclaimer, the term of this patent is extended or adjusted under 35 U.S.C. 154(b) by 343 days.

(21) Appl. No.: 13/465,201

(22) Filed: May 7, 2012

(65) Prior Publication Data

US 2012/0230868 A1 Sep. 13, 2012

Related U.S. Application Data

(62) Division of application No. 12/514,502, filed on Dec. 18, 2009.

(60) Provisional application No. 60/858,944, filed on Nov. 15, 2006, provisional application No. 60/901,007, (Continued)

(51) Int. Cl.
*A61L 2/07* (2006.01)
*A61L 2/20* (2006.01)

(52) U.S. Cl.
CPC .. *A61L 2/07* (2013.01); *A61L 2/208* (2013.01); *A61L 2202/122* (2013.01)
USPC .............. 422/28; 422/292; 422/305; 422/307

(58) Field of Classification Search
CPC ....... A61L 2/0094; A61L 2/0023; A61L 2/07; A61L 2202/122
USPC ........ 422/26–28, 33, 292, 295, 298, 305, 307
See application file for complete search history.

(56) References Cited

U.S. PATENT DOCUMENTS

| 5,711,086 A | 1/1998 | Stubbing |
| 5,804,139 A * | 9/1998 | Lin et al. .................... 422/27 |

(Continued)

FOREIGN PATENT DOCUMENTS

| WO | WO2008061137 | 5/2008 |
| WO | WO2008061139 | 5/2008 |

OTHER PUBLICATIONS

"International Application Serial No. PCT/US07/84667, International Preliminary Report on Patentability", issued May 19, 2009, 11 pgs.

(Continued)

*Primary Examiner* — Timothy Cleveland
(74) *Attorney, Agent, or Firm* — Michael C. Connelly

(57) ABSTRACT

A sterilizing apparatus includes an enclosure defining an interior chamber and a door for accessing the interior chamber. A fluid source communicates with the chamber to supply a working fluid thereto. A heater heats the fluid in the chamber and a pump moves the fluid in the chamber by the heater. A valve communicates with the chamber and with the exterior of the chamber and is configured to vent the fluid in the chamber to the exterior at a pressure of approximately one atmosphere. Such provides superheating and concentrating of the working fluid in the chamber. A method of sterilization includes introducing a working fluid into an interior chamber and circulating the fluid through at least one recirculation loop having a heater for heating the fluid to an operational temperature suitable for killing microorganisms. The method further provides for killing of very high temperature resistant microorganisms.

5 Claims, 5 Drawing Sheets

Related U.S. Application Data filed on Feb. 9, 2007, provisional application No. 60/907,944, filed on Apr. 24, 2007, provisional application No. 60/924,958, filed on Jun. 4, 2007, provisional application No. 60/929,637, filed on Jul. 6, 2007, provisional application No. 60/935,160, filed on Jul. 25, 2007, provisional application No. 60/935,967, filed on Sep. 4, 2007.

(56) References Cited

U.S. PATENT DOCUMENTS

| | | |
|---|---|---|
| 6,161,306 A | 12/2000 | Clodic |
| 6,734,405 B2 | 5/2004 | Centanni et al. |
| 6,880,491 B2 | 4/2005 | Reiner et al. |
| 6,900,421 B2 | 5/2005 | Varma |
| 7,079,759 B2 | 7/2006 | Tokutake |
| 7,113,695 B2 | 9/2006 | Ono |
| 7,115,845 B2 | 10/2006 | Nomura et al. |
| 7,592,500 B2 | 9/2009 | McVey et al. |
| 2004/0057868 A1* | 3/2004 | McVey et al. ............ 422/28 |
| 2006/0251542 A1* | 11/2006 | Sims ............... 422/33 |
| 2007/0145038 A1 | 6/2007 | Reddy et al. |
| 2010/0129157 A1 | 5/2010 | Reddy et al. |
| 2010/0150775 A1 | 6/2010 | Reddy et al. |

OTHER PUBLICATIONS

"International Application Serial No. PCT/US07/84667, Written Opinion of the International Search Authority", issued May 19, 2009, 10 pgs.

International Application Serial No. PCT/US07/84667, Later Publication of International Search Report, issued Sep. 25, 2009, 7 pgs.

\* cited by examiner

APPARATUS AND METHOD FOR STERILIZING ITEMS

CROSS-REFERENCE TO RELATED APPLICATIONS

This is a division of application Ser. No. 12/514,502, filed Dec. 18, 2009 which claims the benefit of U.S. Provisional Application Ser. No. 60/858,944 filed on Nov. 15, 2006; U.S. Provisional Application Ser. No. 60/901,007 filed on Feb. 9, 2007; U.S. Provisional Application Ser. No. 60/907,944 filed on Apr. 24, 2007; U.S. Provisional Application Ser. No. 60/924,958 filed on Jun. 4, 2007; U.S. Provisional Application Ser. No. 60/929,637 filed on Jul. 6, 2007; U.S. Provisional Application Ser. No. 60/935,160 filed on Jul. 25, 2007; U.S. Provisional Application Ser. No. 60/935,967 filed on Sep. 4, 2007; and PCT Application Ser. No. PCT/US07/84667, entitled "Apparatus and Method for Sterilizing Items" each of which is hereby incorporated by reference herein in its entirety. This application is also related to PCT Application Ser. No. PCT/US07/84670, entitled "Heating and Sterilizing Apparatus and Method of Using Same" filed on Nov. 14, 2007, the disclosure of which is also hereby incorporated by reference herein in its entirety.

TECHNICAL FIELD

Aspects of the invention are directed to an apparatus and method for sterilizing items, and more particularly, to sterilizing items for the medical industry using a superheated fluid such as steam.

BACKGROUND

There are many industries interested in providing items that are free from bacteria, viruses, fungi, spores, and other pathogenic microorganisms, including the food industry, the medical industry, waste management industry, and many others. For example, hospitals, doctor offices, dentist offices, veterinary offices and other providers of medical services to humans or animals require sterile items, such as medical instruments, surgical linens, etc., free from pathogenic microorganisms.

Although there are several approaches for sterilizing items, including heat sterilization, chemical sterilization, radiation, etc., heat sterilization is the most common approach to providing sterile items. Several heat sterilization procedures are currently in practice and include both wet and dry sterilization. Wet heat sterilization is considered the most dependable procedure for the destruction of microorganisms and typically includes water (steam) as the working fluid for achieving sterilization. Dry sterilization, on the other hand, uses a dry gas as its working fluid, is less efficient, and typically requires higher temperatures and longer exposure times to achieve sterile conditions. For example, steam sterilization uses pressurized steam at 121° C.-134° C. for about thirty to forty minutes while dry sterilization typically requires a temperature of between 160° C.-170° C. for an exposure time of between two to four hours. Accordingly, the various industries, including the medical industry, focus primarily on wet sterilization procedures.

Conventionally, in hospitals, doctor offices, etc., the commonly employed procedure for wet sterilization is autoclaving. In autoclaving, the item(s) to be sterilized, such as, for example, bandages, operating gowns and other linens, surgical knives, forcipes, and other instruments, are positioned within a chamber of an autoclave. Saturated steam generated by, typically, an external steam generator (e.g., boiler) is introduced into the chamber and has a temperature of approximately 100° C. Because it is difficult to kill microorganisms at this temperature in a relatively short period of time, the pressure in the chamber may be increased so as to raise the temperature of the steam. For example, for saturated steam to have a temperature of approximately 121° C., the chamber must be pressurized to approximately 30 psi. The pressure required to reach higher temperatures correspondingly increases. For example, for the steam to have a temperature of approximately 134° C., the chamber must be pressurized to approximately 44 psi. Once the operational temperature/pressures has been reached, the conditions are maintained within the chamber for a prescribed period of time to achieve sterilization of the items. After the sterilization period, the pressure in the chamber is released so as to allow removal of the sterilized items. Use of an autoclave, while being primarily associated with the destruction of microorganisms, may be used in other applications as well. For example, autoclaves may be used in various metallurgy processes, ceramic processes, etc.

While autoclaving has been generally successful for its intended purpose of sterilizing various items, including items for the medical industry, there are some drawbacks to this practice. For example, autoclaves effectively operate as pressure vessels and thus their design and use may be regulated by various local, state and/or federal regulations or standards for ensuring proper and safe operation thereof. Meeting the standards often results in the autoclave having a relatively heavy, bulky design with increased overall costs. Additionally, autoclaves typically require relatively large steam generators. In this regard, because the autoclave operates at increased pressures, a significant amount of steam has to be generated to reach saturated conditions inside the chamber at the elevated temperatures. The amount of steam required at the increased pressures mandates that relatively large steam generators be utilized. For relatively small autoclaves (e.g., small office use), the steam generators may be built into the autoclave or located immediately adjacent to the autoclave. Such autoclaves having the steam generator therewith tend to be heavy and bulky. In addition, the relatively large steam generators increase the table, floor, or countertop space (i.e., machine footprint) occupied by the autoclave.

For relatively large autoclaves, the steam generator may not be positioned locally (i.e., integrated into the autoclave or immediately adjacent the autoclave), but instead may be remotely located. For example, hospitals, universities, and other large building, campuses, etc. may have a centralized boiler that provides steam to many locations throughout the larger structure or community. In this regard, piping or other conduits carry the steam from the boiler throughout the larger structure. Because the steam is transported over appreciable distances, such systems are susceptible to heat loss, which affects the quality of the steam; leaks, which result in a loss of pressure, mass flow, etc. and require frequent and costly maintenance; and other factors which diminish the effectiveness of such remotely located steam generators. Furthermore, dedicated ports for accessing the steam lines are predetermined (e.g., during construction of the building, campus, etc.) so that the location of the autoclave within a hospital room, laboratory, etc. is limited. This in turn limits the design considerations for the space in which the autoclave is to be located. Attempts to relocate a steam port are difficult and costly and are thus generally discouraged by maintenance personnel and the like.

In addition to the above, autoclaves lack the robustness of sterilizing devices required by current applications and also lack the robustness to meet the future challenges of providing sterilized items free from microorganisms. For example, autoclaves typically utilize only one type or mode of sterilization, i.e., wet heat sterilization, and typically operate using only a single working fluid, i.e., water. However, there are instances when other sterilization techniques may be desired. For example, it may be desired to use dry heat sterilization to kill certain microorganisms or with certain items suitable for dry heat sterilization. In such cases, the autoclave is incapable of operating in a dry heat sterilization mode and a completely separate device is typically required. Having two separate devices increases costs and may utilize valuable table, floor, or countertop space. Additionally, operators must be appropriately trained to operate multiple, perhaps significantly different devices. Such situations may result in increased operator error.

Furthermore, in some applications, it may be desirable to augment wet heat sterilization with other types of sterilization. For example, in some applications it may be desirable to use radiation, including ultraviolet (UV) radiation, infra red (IR) radiation, x-rays, microwaves, and other forms of radiation, in combination with wet heat sterilization processes. Moreover, in other applications, it may be desirable to use a form of chemical sterilization in combination with a wet heat sterilization process. With autoclaves, however, incorporating such additional or auxiliary sterilization is problematic due to the need to pressurize the chamber. Thus, any additional sterilization using one of these other processes requires a separate device and separate processing steps to achieve such additional sterilization.

Perhaps a more serious flaw of autoclaves, however, is that autoclaves are incapable of operating over a selected temperature range. Instead, autoclaves are typically designed to operate at a predetermined temperature. More particularly, autoclaves typically operate at either 121° C. or 134° C. depending on the particular sterilization application. Unfortunately, many in the scientific community anticipate that in the future, higher temperatures will be required to kill certain microorganisms. For example, sterilization procedures at approximately 140° C., 180° C., or even higher may be required to kill resistant bacteria, viruses, and other pathogenic microorganisms. For higher wet heat temperatures, the corresponding pressure in the autoclave must significantly increase. Current autoclaves, however, are not readily modifiable so as to operate at these elevated temperatures. More particularly, to get to these elevated temperatures, the chamber of the autoclave will have to be pressurized to approximately 52 psi, 145 psi, respectively, or higher. Current autoclaves simply are not designed to operate at these elevated pressures. Accordingly, current autoclaves will have to be summarily replaced with new, larger, and heavier autoclaves rated for the elevated pressures and temperatures. Such wholesale replacement would be cost prohibitive to many facilities for which sterilization is essential. In addition to the above, autoclaves may pose a health hazard, as more fully discussed at www2.umdnj.edu/eohssweb/aiha/accidents/autoclave.htm, the disclosure of which is incorporated by reference herein in its entirety.

The use of superheated steam at atmospheric pressures has been proposed in other, non-medical industrial applications. By way of example, U.S. Pat. No. 6,161,306 is directed to apparatus and methods of drying a load of moist fibrous material (e.g., a load of laundry) using superheated steam at atmospheric pressures. The '306 patent, however, is devoid of any disclosure or appreciation of aspects relating to antimicrobial effects. It is believed that the apparatus disclosed in the '306 patent is incapable of generating a high percentage of steam within the enclosure. As discussed below, however, for antimicrobial applications similar to that for which autoclaves are typically used, high concentrations of steam may be required.

U.S. Pat. No. 7,113,695 is directed to heat treating various items, such as various odoriferous food items, wherein superheated steam and a dry distillation gas is recirculated through a chamber holding the items and the steam and dry distillation gas are channeled through a deodorizer filter to deodorize the steam and gas. It is believed that due to the presence of the dry distillation gas, the apparatus would be incapable of achieving a high concentration of steam within the chamber.

U.S. Pat. No. 5,711,086 is directed to an open system for continuously drying moist materials. It is also believed that the apparatus described in the '086 patent will be incapable of achieving a high concentration of steam within its chamber. U.S. Pat. No. 6,900,421 is directed to a sterilizing apparatus using microwave heating for generating superheated steam. U.S. Pat. No. 6,880,491 is directed to generating superheated steam using hydrogen peroxide and a combustible fluid, wherein the combustion process decomposes the hydrogen peroxide to produce superheated steam. U.S. Pat. No. 7,115,845 is directed to a superheated steam generator that uses electromagnetic induction to produce the superheated steam. U.S. Pat. No. 7,079,759 is directed to a device for generating saturated steam not superheated steam.

Accordingly, there is a need for an improved sterilizing apparatus and method for sterilizing items that overcomes these and other drawbacks of current autoclaves and prior art systems. More particularly, there is a need for a sterilizing apparatus and associated method that can operate at atmospheric pressure; that include localized steam generators that are smaller and lighter than conventional steam generators; that are versatile; that are capable of operating over a relatively large temperature range; that are capable of producing a high concentration of steam within the chamber; that are capable of operating in different modes or in combination with a host of other sterilization procedures; and that are capable of heating and concentrating the fluid continuously or intermittently independent of any pressure increase or decrease in the chamber.

SUMMARY

A sterilizing apparatus for sterilizing items includes an enclosure defining an interior chamber that is adapted to hold the items being sterilized therein, and at least one door for selectively accessing the interior chamber. A fluid source is in fluid communication with the interior chamber and supplies a working fluid to the chamber for sterilizing the items. The sterilizing apparatus further includes a heater for heating the fluid in the interior chamber and a pump for moving the fluid in the interior chamber so as to be in thermal communication with the heater. A valve is in fluid communication with the interior chamber and also in fluid communication with the exterior of the interior chamber and is configured to vent the fluid in the chamber to the exterior at a pressure of approximately one atmosphere. In this way, the sterilizing apparatus is capable of heating the fluid in the interior chamber to an operational temperature suitable for killing microorganisms and sterilizing the items located therein while maintaining the pressure within the interior chamber at approximately one atmosphere.

In one embodiment, the fluid source includes a steam generator for supplying saturated steam to the interior chamber as the working fluid and the heater causes the saturated steam to become superheated. In an alternate embodiment, the fluid source may be a dry gas source for supplying a dry gas to interior chamber as the working fluid. For example, the dry gas source may include a source of air, nitrogen, carbon dioxide, carbon-containing gases, noble gases, chlorides, bromides, or other suitable dry gases. In still a further embodiment, the fluid source may include a boiler for supplying the vapor of a liquid chemical to the interior chamber as the working fluid. For example, the liquid chemical may include paracetic acid, formaldehyde, propyleneoxide, hydrogen peroxide, glutaraldehyde, pesticides, and sodium compounds like benzanates. Thus, the sterilizing apparatus is capable of operating with a wide range of working fluids including water, nitrogen, air, carbon dioxide, and other liquids, gases, and mixtures or combinations thereof.

In one embodiment, the heater may be the coil-in-coil heater disclosed in U.S. Publication No. 2007/0145038, the disclosure of which is incorporated by reference herein in its entirety. The heater may also by those disclosed in PCT application Ser. No. PCT/US07/84670, entitled "Heating and Sterilizing Apparatus and Method of Using Same" filed on Nov. 14, 2007, the disclosure of which is also incorporated by reference herein in its entirety. The heater may have a power rating of between approximately 1 kilowatt and approximately 4 kilowatts and be controllable so as to heat the fluid in the interior chamber to a temperature no greater than approximately 200° C. In another embodiment, a higher power heater may also be used that is capable of heating the fluid in the interior chamber to very high temperatures, such as about 1,500° C. with suitable insulation in the chamber. In one embodiment, the sterilizing apparatus includes at least one recirculation loop having at least one inlet in fluid communication with the interior chamber and at least one exit in fluid communication with the interior chamber. The pump causes the fluid in the interior chamber to flow through the at least one recirculation loop and the heater is in thermal communication with the loop for heating the fluid flowing therethrough. The exits of the recirculation loop may be disposed uniformly about the interior chamber. In one embodiment, there are a plurality of recirculation loops, with each loop having its own pump and heater for causing flow through the loop and for heating the fluid flowing therethrough.

The interior chamber and recirculation loop are sealed from the environment such that substantially no air or other environmental fluids may enter the interior chamber. In this regard, in one embodiment, the pump may be a bellows pump that provides enhanced sealing relative to the environment. The bellows pump includes a housing having at least one sub-housing that defines a bore. A piston may be disposed in the bore and capable of reciprocating movement therein between a first position and a second position. A bellows has a first end coupled to the sub-housing and a second end coupled to the piston to define a bellows chamber capable of drawing fluid from the interior chamber and expelling the fluid back to the interior chamber through the heater. The bellows pump may include a motor and piston rod for actuating the piston between the first and second positions. In addition, the bellows pump may be configured such that when a first group of sub-housings have pistons in the first position, a second group of sub-housings have pistons in the second position. A bellows pump may also be used to pulse the fluid in the interior chamber.

In another embodiment, a radiation or ultrasound source may be positioned in the interior chamber for exposing the items to be sterilized to radiation or ultrasound. Such an embodiment further enhances the sterilization process. By way of example, an ultraviolet (UV) light source, infrared (IR) light source, or radiofrequency (RF) generator may be positioned in the interior chamber for exposing the items to UV, IR, or RF radiation. A gamma source may also be positioned in the interior chamber for exposing the items to gamma rays.

In one embodiment, an apparatus includes a fluid tight interior chamber containing a first fluid and at least one one-way valve in fluid communication with the chamber, wherein at least one of the one-way valves is configured to open at a pressure of approximately one atmosphere. A fluid source is in fluid communication with the interior chamber for introducing a working fluid therein. Such a configuration allows the apparatus to achieve a concentration of the working fluid in the interior chamber of greater than approximately 85%, and perhaps greater than approximately 95%. Achieving such high concentrations are done while maintaining a pressure of approximately one atmosphere.

In another embodiment a multi-mode sterilizing apparatus for sterilizing items includes an enclosure defining an interior chamber for holding the items to be sterilized and a door for selectively accessing the interior chamber. A first fluid source is in selective fluid communication with the interior chamber for supplying a first working fluid thereto. A second fluid source is also in selective fluid communication with the interior chamber for supplying a second working fluid thereto. The sterilizing apparatus further includes a heater for heating the fluid in the interior chamber and a pump for moving the fluid in the interior chamber so as to be in thermal communication with the heater. A valve is in fluid communication with the interior chamber and also in fluid communication with the exterior of the interior chamber and is configured to vent the fluid in the chamber to the exterior at a pressure of approximately one atmosphere. The sterilizing apparatus operates in a first mode of sterilization when the first fluid source is in fluid communication with the interior chamber and operates in a second sterilization mode when the second fluid source is in fluid communication with the interior chamber. By way of example, the first mode of sterilization may include wet heat sterilization, dry heat sterilization, or chemical sterilization, and the second mode of sterilization may include another of wet heat sterilization, dry heat sterilization or chemical sterilization. In another embodiment, the first and second modes may be differentiated by operational temperature. Thus, the first mode of sterilization may include an operational temperature of less than approximately 135° C., and the second mode of sterilization may include an operational temperature of greater than approximately 160° C. One or both of the first or second modes of sterilization may also accommodate intermediate temperatures.

A method of sterilization includes introducing a working fluid into an interior chamber holding the items to be sterilized and circulating the fluid in the interior chamber through at least one fluid tight recirculation loop having a heater in thermal communication therewith for heating the fluid up to an operational temperature suitable for killing microorganisms. The method may further provide venting of the fluid from the interior chamber so as to maintain the pressure therein at approximately one atmosphere. The items to be sterilized are then exposed to the heated fluid in the interior chamber to effectuate sterilization thereof.

In one embodiment, steam is introduced into the interior chamber as the working fluid. In another embodiment, a dry gas in introduced into the interior chamber as the working fluid. In one embodiment, the fluid in the interior chamber may be heated to a temperature no greater than about 200° C. Higher temperatures, however, are possible. The fluid in the interior chamber may be circulated through a plurality of loops and may further be restricted so at to flow in a unidirectional manner through the recirculation loops. In addition, the sterilization process may include thermal cycling wherein the temperature of the fluid is cooled, such as actively or passively, to a temperature below the saturation temperature of the fluid so that condensation forms in the interior chamber. Once condensation forms, the fluid may be heated back up to the operational temperature. This thermal cycling may be repeated as desired. A bellows pump may be used to circulation the fluid in the interior chamber as well as to pulse the fluid in the chamber.

A method for increasing the concentration of a working fluid within a chamber to a preset valve, wherein the chamber includes a first fluid includes introducing the working fluid to the chamber at a concentration greater than or equal to the preset value, heating the mixture of the working fluid and the first fluid, and venting a portion of the mixture of the working fluid and the first fluid from the chamber. The method further includes preventing substantially any fluid external to the chamber from entering the chamber. The introducing, heating, venting, and preventing steps may be repeated until the concentration of the working fluid in the chamber reaches the preset value.

In another embodiment, a multi-mode sterilization method includes introducing a first working fluid into an interior chamber holding a first group of items to be sterilized and exposing the first group of items to the first working fluid in a first mode of sterilization. The method further includes introducing a second working fluid into the interior chamber holding a second group of items to be sterilized and exposing the second group of items to the second working fluid in a second mode of sterilization. The first mode of sterilization may include wet heat sterilization, dry heat sterilization, or chemical sterilization, and the second mode of sterilization may include another of wet heat sterilization, dry heat sterilization or chemical sterilization. The first and second modes may also be differentiated by operational temperature. Thus, the first mode of sterilization may include an operational temperature of less than approximately 135° C., and the second mode of sterilization may include an operational temperature of greater than approximately 160° C. One or both of the first or second modes of sterilization may also accommodate intermediate temperatures.

These and other objects, advantages and features of the invention will become more readily apparent to those of ordinary skill in the art upon review of the following detailed description taken in conjunction with the accompanying drawings.

BRIEF DESCRIPTION OF THE DRAWINGS

The accompanying drawings, which are incorporated in and constitute a part of this specification, illustrate embodiments of the invention and, together with a general description given above, and the detailed description given below, serve to explain aspects of the invention.

DETAILED DESCRIPTION

Figure 1:
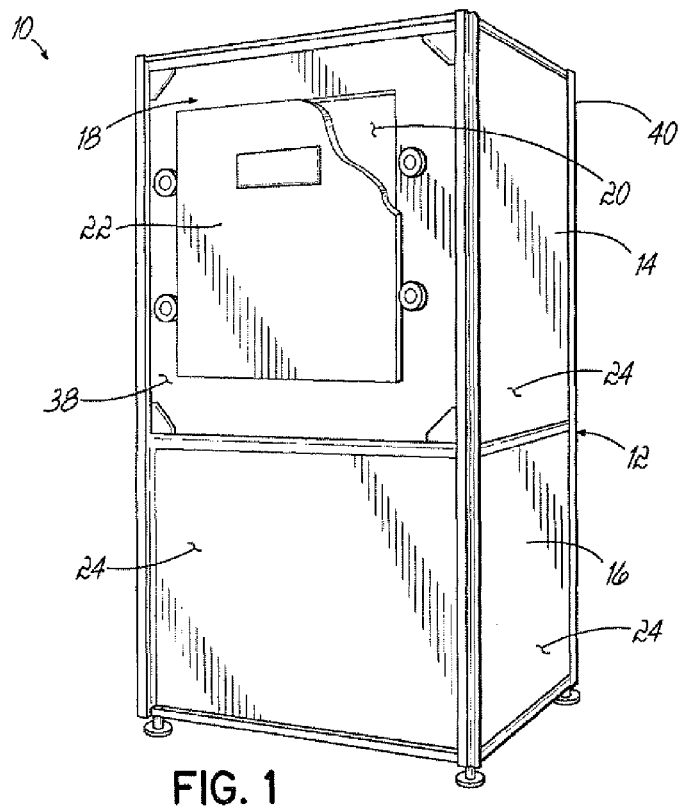
FIG. 1 is a perspective view of a sterilizing apparatus in accordance with one embodiment of the invention.

In reference to the figures, and more particularly, in reference to FIG. 1, an exemplary embodiment of a sterilizing apparatus 10 in accordance with aspects of the invention is illustrated. Sterilizing apparatus 10 may be configured as a stand-alone device and includes a generally rectangular cabinet 12 having an upper portion 14 and a lower portion 16. Although sterilizing apparatus 10 is illustrated as a stand-alone device, it should be recognized that other configurations are possible, depending on the specific application and other factors, and embodiments of the invention should not be limited to that shown in FIG. 1. For example, smaller, tabletop configurations are contemplated to be within the scope of the invention. The cabinet 12 provides sufficient structure to house and support the various elements of the sterilizing apparatus 10, as discussed in more detail below. The upper portion 14 includes an enclosure 18 defining an interior chamber 20 and a door 22 for selectively accessing the interior chamber 20. The door 22 may include standard door seals as are generally known in the art for sealing the door 22 to the apparatus 10. As discussed below, because there is no pressure differential between the interior and exterior of the interior chamber 20, should the door 22 be inadvertently opened during a sterilization cycle, there is no pressurized steam that will exit and cause damage. Moreover, in embodiments in accordance with the invention, the door 22 may be quickly opened, which is in contrast to the standard pressure release cycle required in autoclaves. The interior chamber 20 is adapted to hold the items (not shown) to be sterilized, such as, for example, various medical instruments, surgical linens, etc. The lower portion 16 of the cabinet 12 houses and supports the elements or devices that facilitate operation of the sterilizing apparatus 10. Thus, as discussed below, the lower portion 16 may include a water source, steam generator, pump, heater, and other devices that make the sterilizing apparatus operational. The cabinet 12 may include removable cover plates or panels 24 for presenting an aesthetically pleasing appearance to the sterilizing apparatus 10, but yet allow access to the components of the apparatus 10 for repair, replacement, etc.

Figure 2:
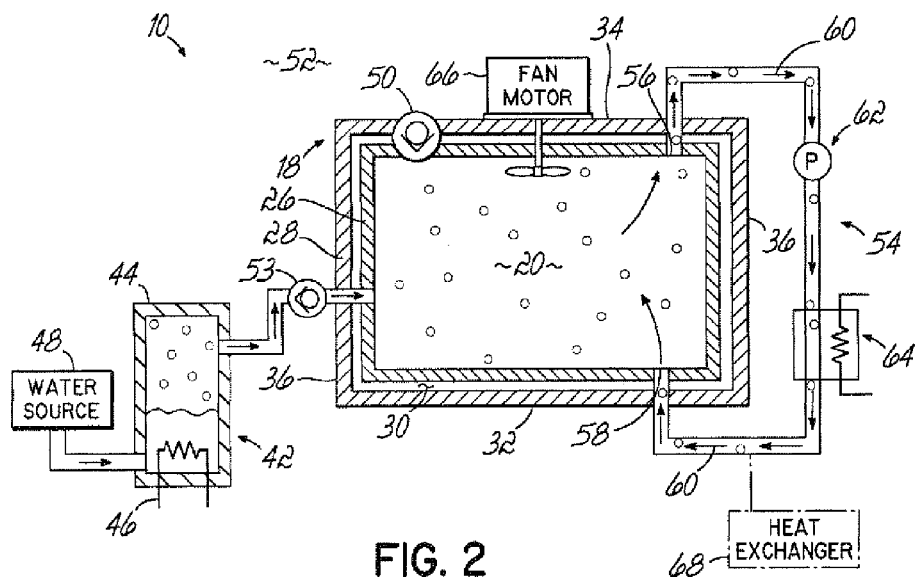
FIG. 2 is a diagrammatic illustration of the sterilizing apparatus shown in FIG. 1.

The components and operation of sterilizing apparatus 10 are perhaps best understood in reference to the diagrammatic illustration shown in FIG. 2, in which like reference numerals refer to like features shown in FIG. 1. In one embodiment, the enclosure 18 may have a double walled construction that effectively reduces heat loss from the enclosure 18 so as to, in essence, provide an insulation layer about its outer bounds. In this regard, the enclosure includes an inner wall 26, an outer wall 28, and an open gap or void 30 separating the two walls 26, 28. The void 30 may be filled with air or other inert gas that reduces heat transfer from the enclosure. Alternatively, any air or gas in the void 30 may be removed so effectively create a vacuum between the two walls 26, 28 and eliminates conduction and convection modes of heat transfer away from the enclosure 18. Referring to FIGS. 1 and 2, the enclosure 18 may have a generally rectangular shape defining a bottom wall 32, at top wall 34, a pair of side walls 36, a front wall 38, and a back wall 40. The invention is not limited to the enclosure 18 having such a rectangular shape as the enclosure 18 may have a wide range of shapes, such as a generally spherical shape or other suitable shapes. In addition, as is generally known in the art, the interior chamber 20 defined by enclosure 18 may include one or more walls, shelves, racks, etc. for separating the interior chamber 20 into a plurality of compartments.

The enclosure 18 may be formed from any suitable material including aluminum, stainless steel, other suitable metals, ceramics like alumina, zirconia, silica and mixtures thereof, or various engineering plastics such as polycarbonates, polyurathanes, high temperatures plastics like Norel®, Zytel®, or other suitable plastics. As discussed below, the sterilizing apparatus 10 operates at substantially atmospheric pressure. Accordingly, the enclosure 18 does not have to be designed to withstand increased pressures, and may be formed from a wider selection of materials relative to existing autoclaves. However, the material for the enclosure 18 should be selected so as to withstand high temperatures without loss of function, structural integrity, etc. For example, in one embodiment, the material for the enclosure 18 may withstand temperatures as high at 200° C. This value, however, depends on the specific application. Other applications may require that the enclosure withstand temperatures lower or higher than this value. Those of ordinary skill in the art will recognize how to select the material for enclosure 18 to meet the requirements of the specific application.

In one embodiment, the sterilizing apparatus 10 includes a steam generator 42 in fluid communication with the interior chamber 20 of enclosure 18 for introducing saturated steam therein. Although not shown in FIG. 1, the steam generator 42 may be located in the lower portion 16 of the cabinet 12. The steam generator 42 generally includes a housing 44 containing water and a heater, shown diagrammatically at 46, for heating the water to its boiling point (about 100° C.) to generate saturated steam that is introduced into interior chamber 20. A water source 48, such as a tank, bag, etc., may be in fluid communication with the steam generator 42 to provide a substantially continuous supply of water to the steam generator 42. Such a steam generator 42 is generally well known in the art and is commercially available. The size or capacity of the steam generator 42 may depend on several application-specific factors. By way of example, one metric for determining the size of the steam generator 42 is the desired flow rate of saturated steam into the interior chamber 20. In some applications, it may be desirable to have a flow rate of steam between approximately 10 ml/min and approximately 100 ml/min for a chamber having a size of about 1-9 cubic feet. If the chamber is smaller or larger then the flow rate ranges may be adjusted accordingly. The desired flow rate into the chamber may then be used to size the steam generator 42, determine the wattage of the heater 46, etc. so as to produce the desired result. One or ordinary skill in the art will recognize how to size the steam generator 42 to produce the desired flow rate into the interior chamber 20. For example, to generate a flow rate of steam in the range identified above, a steam generator 42 having about a one-half gallon housing 44 and about a 0.6 kW heater 46 may be suitable. Those of ordinary skill in the art will recognize other metrics for sizing the steam generator 42 and the invention is not limited to that described above.

In stark contrast to autoclaves, the sterilizing apparatus 10 is configured to operate at substantially atmospheric pressure. For example, the sterilizing apparatus 10 may operate in the range of +/−10% of atmospheric pressure. To this end, the sterilizing apparatus 10 includes a one-way valve (e.g., check valve) 50 that provides a fluid communication path between the interior chamber 20 and the environment 52 external to the interior chamber 20. The one-way valve 50 effectively operates as a vent to allow (slightly pressurized) fluid (e.g., air, steam, air-steam mixture, etc.) to flow out of the interior chamber 20 and be replaced with the working fluid of interest (e.g., steam, dry gas, etc.), as discussed in more detail below. In particular, the one-way valve 50 may be designed so as to open (i.e., allow venting) when the pressure in the interior chamber 20 slightly exceeds atmospheric pressure. For example, the one-way valve 50 may be designed to open at about 0.1 psig. The valve 50 may also be designed to permit the cracking pressure to be selectable or adjustable as dictated by the specific application. In this way, the enclosure 18 is not capable of withstanding increased pressures and the pressure within the interior chamber 20 remains substantially at atmospheric pressure during the operation of the sterilizing apparatus 10. While the valve 50 allows fluid inside the interior chamber 20 to be evacuated, the one-way valve 50 also prevents air or other environmental gases, fluids, etc. to enter the interior chamber 20. Such one-way valves 50 are well known and well understood in the art and are commercially available from many vendors. The valve 50 may be electronically actuated, or alternatively be pneumatic, spring-loaded, or mechanically actuated with a fluid type of actuator or electrical input. Those of ordinary skill in the art will recognize other valves which may be used in accordance with the invention. Such one-way valves 50 are in contrast to any venting valve in an autoclave (e.g., gravity fed types), which are typically set by a predetermined weight or pressure (similar to household pressure cooker valve). Unlike any venting system in conventional autoclaves, the one-way valve 50 provides a fluid concentration function, as explained in more detail below.

The one-way valve 50 may be sized so as to allow the fluid inside interior chamber 20 to vent without choking or otherwise restricting the flow therefrom. For example, the one-way valve 50 may permit a flow rate through the valve of greater than about 1 ml/hr. The one-way valve 50 should also be rated to handle fluids at the desired operating temperature of the sterilizing apparatus 10 (e.g., 121° C., 134° C., or higher). One-way valve 50, as well as other exhaust points that provide communication between the interior and exterior of chamber 20, may include a low-porosity filter, such as a HEPA filter rated for particles sized appropriately for the specific application (e.g., micrometer-sized particles), to reduce and eliminate potential contamination due to such a release. Such exhaust points from interior chamber 20 may further include a heater for burning off any microorganisms before being vented.

In addition to the one-way valve 50, the sterilizing apparatus 10 may include an optional one-way valve 53 positioned intermediate the interior chamber 20 and the steam generator 42. The one-way valve 53 provides unidirectional flow of steam from the steam generator 42 and to the interior chamber 20. The valve 53, however, prevents the flow of fluid from the interior chamber 20 and toward the steam generator 42. The one-way valve 53 may be similar to valve 50 and be sized so as to accommodate the desired flow rate of steam from the steam generator 42. The one-way valve 53 should also be rated to handle the temperature of the fluids flowing therethrough (e.g., 60° C. for saturated steam).

To facilitate generation of superheated steam within the interior chamber 20 of enclosure 18, the sterilizing apparatus 10 includes a recirculation loop 54 having an inlet 56 in fluid communication with interior chamber 20 and an exit 58 also in fluid communication with interior chamber 20. Fluid from within the interior chamber 20 flows through the inlet 56, through the recirculation loop 54, and back into the interior chamber 20 through the exit 58, as illustrated by arrows 60. To promote such a flow of fluid through the recirculation loop 54, the sterilizing apparatus 10 may include a pump 62 for drawing fluid into the recirculation loop 54 and expelling the fluid in the recirculation loop 54 back into the interior chamber 20. The pump 62 should be selected so as to accommodate the particular working fluid of the sterilizing apparatus 10. For example, the pump 62 should accommodate saturated steam, air, superheated steam, nitrogen, carbon dioxide, other dry gases, other saturated or supersaturated liquids, and combinations of these fluids. The pump 62 should also be rated to handle fluids at the desired operating temperature of the sterilizing apparatus 10 (e.g., 121° C., 134° C., or higher). Moreover, the pump 62 should be selected to as to permit a suitable flow rate through the recirculation loop 54. For example, the pump 62 may permit a flow rate through the recirculation loop 54 of greater than about 1 ml/hr. Those of ordinary skill in the art will understand how to select an appropriate pump 62 given the parameters of a particular application.

While the pump 62 promotes flow through the recirculation loop 54, a heater 64 may be disposed in the recirculation loop 54 for heating the fluid flowing therethrough. For example, in one embodiment, the heater 64 heats saturated steam, such as from steam generator 42, to produce superheated steam within interior chamber 20. In one exemplary embodiment, the heater 64 may be the coil-in-coil heater fully disclosed in U.S. Publication No. 2007/0145038, or that disclosed in PCT Application. Ser. No. PCT/US07/84670, entitled "Heating and Sterilizing Apparatus and Method of Using Same" filed on Nov. 14, 2007, each of the disclosures being incorporated by reference herein in their entirety. Accordingly, the details of the coil-in-coil heater will not be repeated here. In any event, the heater 64 may be configured to heat the fluid flowing through the recirculation loop 54 to the operating temperature of the sterilizing apparatus 10 (e.g., 121° C., 134° C., or higher). For example, the heater 64 should accommodate and heat saturated steam, air, superheated steam, nitrogen, carbon dioxide, other dry gases, other saturated or supersaturated liquids, and combinations of these fluids to the desired operating temperature. Moreover, the heater 64 should be selected to heat these fluids at the design flow rate through recirculation loop 54, as determined, for example, by pump 54. In an exemplary embodiment, it is contemplated that a 1-4 kW heater should suffice in most applications to heat the fluid to no greater than about 200° C. However, those of ordinary skill in the art will understand how to select an appropriate heater 64 given the parameters of a particular application. Furthermore, the heater 64 disclosed in U.S. Publication No. 2007/0145038 or PCT application Ser. No. PCT/US07/84670, entitled "Heating and Sterilizing Apparatus and Method of Using Same" filed on Nov. 14, 2007 are exemplary and those of ordinary skill in the art may recognize other heaters 64 which may be used for heating the fluid flowing through recirculation loop 54. Therefore, the invention is not limited to the heater described in these references and a wider range of heaters is contemplated to be within the scope of the invention.

In operation, various items that are to be sterilized, such as various medical instruments, surgical linens, etc., are inserted into the interior chamber 20 of enclosure 18 through, for example, door 22. The door 22 may be closed and secured to the enclosure 18 in a fluid tight manner. The steam generator 42 is energized to heat the water from source 48 and produce saturated steam, which is then introduced into the interior chamber 20 as the working fluid. In one embodiment, air initially fills the interior chamber and as saturated steam enters the chamber 20 from steam generator 42, a mixture of steam and air fills the chamber 20. The pump 62 and heater 64 are also energized to initiate a flow of the air/steam mixture through the recirculation loop 54 wherein the mixture is heated. As the air/steam mixture becomes heated, the pressure starts to increase within the interior chamber 20. Consequently, the one-way valve 50 opens and vents the air/steam mixture from the interior chamber 20 to the exterior of the interior chamber 20 through the valve 50 to maintain the pressure therein at approximately one atmosphere. The flow of fluid in interior chamber 20 may provide benefits for cleaning or sterilizing certain medical instruments such as endoscopes, tubes (thin and thick), and other hard to clean, intricate medical and non-medical devices. In this regard, such instruments may be positioned generally parallel to an outlet 58 that that the superheated fluid may flow through the interior of the item (e.g., through a lumen of the item). Conventional autoclaves are generally unable to orient such items in the chamber to enhance sterilization of hard to clean items.

In another aspect in accordance with embodiments of the invention, the sterilizing apparatus 10 may be capable of providing a very high concentration of steam in the interior chamber at the about one atmosphere of pressure. In general, for sterilizing purposes it is considered desirable to have a very high concentration of steam in the sterilizing chamber. For example, it is believed that autoclaves and other sterilizing apparatus should have a concentration of steam in the chamber be greater than about 85%, and more preferably, greater than about 95%. As provided at www.spsmedical.com/education.php?page=article&view=21&doprint=true, the AAMI guidelines state that steam quality, purity and quantity can be affected by the design, use and maintenance of the overall steam system. Steam systems should be designed to ensure that the steam delivered to the sterilizer is saturated steam having a steam quality of 97% to 100%. Steam of poor quality can contribute to wet packs and to sub-optimal steam sterilization cycles that might or might not be identified by biological monitoring. In certain circumstances, house steam from hospital steam boiler systems, for example, might not be acceptable for sterilization processes due to the design of the overall system and the type and method of using boiler feed water treatment chemicals. For autoclaves, obtaining such a high concentration of steam in the chamber is typically achieved by applying vacuum pressure thereto to remove the initial air/gases therein. However, removal of nearly all the initial gases contained within the chamber has proven problematic and the ability of autoclaves to provide very high concentrations of steam is tenuous. In this regard, it is believed that the inability to produce a high concentration of steam in the chamber is a primary contributor to the failure rate of autoclaves.

The sterilizing apparatus 10 may be configured to achieve such a high concentration of the working fluid (e.g., steam) in the interior chamber 20. Additionally, the sterilizing apparatus 10 may achieve these high concentrations without applying any vacuum pressure. To this end, because the enclosure 18 and recirculation loop 54 are fluid-tight, i.e., no air or other fluid from the surrounding environment 52 may enter the sterilizing apparatus 10 after the door 22 is closed, and because only pure steam is introduced into the interior chamber 20 from steam generator 42, the concentration of steam in the interior chamber 20 steadily increases from essentially zero and toward substantially 100% steam over a certain period of time. As noted above, the fluid in the chamber, which may initially be a low concentration of steam fluid, is evacuated from the interior chamber 20 through valve 50 as it is heated. This fluid is then replaced with pure steam from steam generator 42. Thus, the concentration of the steam in the interior chamber will increase toward 100% steam. After a suitable period of time, the concentration of steam in the interior chamber 20 will become high and approach the concentration of the steam entering the chamber 20 (e.g., 100%). The sterilizing apparatus 10 should be warmed up so that the concentration of steam in the interior chamber 20 is greater than about 85%, and more preferably greater than about 95%. The invention is not limited as it is believed that the concentration of steam in the interior chamber 20 can easily reach 99-100% given a sufficient, but reasonable amount of warm-up time. Again, this process of going from essentially zero steam to a high concentration of steam occurs at approximately atmospheric pressure, due to the venting through the one-way valve 50. It should be recognized that although in the embodiment described above, pure steam is fed to interior chamber 20 from steam generator 42 so that the concentration of steam approaches 100%, the invention is not so limited. The concentration of the input may vary from pure steam so that the maximum concentration of steam capable of being achieved in interior chamber 20 is less than 100%.

In addition, because the air, steam, or both flow through the recirculation loop 54 and heater 64, the fluid eventually reaches the desired operating temperature of the sterilizing apparatus 10. Thus, for example, the steam that eventually fills the interior chamber 20 may reach a temperature of 121° C., 134° C., or higher temperatures, as dictated by the specific application. Accordingly, after this initial warm-up period, a high concentration steam at temperatures sufficient to kill microorganisms and at substantially atmospheric pressure exists within the interior chamber 20. At these temperatures (above 100° C.) and pressures (one atmosphere), the steam is superheated steam. The interior chamber 20 may be maintained at this operational temperature and pressure for a specified amount of time depending on the particular application. This time may be determined so that the bacteria, viruses, spores, prions, and other microorganisms on the items located in the sterilizing apparatus 10 are destroyed. This time may be determined by various federal or state health codes, or otherwise determined as recognized by those of ordinary skill in the art.

While the diagram of FIG. 2 encompasses the broad concepts in accordance with aspects of the invention, various modifications are also within the scope of the invention. By way of example, while FIG. 2 illustrates a single inlet 56 and single outlet 58 to a single recirculation loop 54, other configurations are possible. For example, there may be multiple inlets 56 to a single recirculation loop 54 or multiple outlets 58 to recirculation loop 54. Thus, in one embodiment, the multiple outlets 58 to recirculation loop 54 may be uniformly spaced about the interior chamber 20. More specifically, an outlet 58 may be located at approximately the midpoint of each of the walls of the enclosure 18 (e.g., walls 32-40). Such a spacing in the outlets 58 provides a more uniform distribution of superheated steam within the interior chamber 20. To further prevent or reduce the likelihood of temperature variations or steam quality variations (e.g., non-uniformities) within interior chamber 20, the sterilizing apparatus 10 may include one or more recirculation fans, shown diagrammatically at 66, that effectively stirs the fluid within the interior chamber 20. Such recirculation fans 66 are generally known in the art and are commercially available from various vendors. The size of the recirculation fan(s) 66 may depend of the specific application, including the size of the interior chamber 20, but is readily determinable by those of ordinary skill in the art. Furthermore, while a single recirculation loop 54 is shown in FIG. 2, it should be recognized that sterilizing apparatus 10 may include multiple independent or interconnected recirculation loops.

Operation of the sterilizing apparatus 10 as described above may also be modified in a manner within the scope of the invention. For example, the air that is initially in the interior chamber 20 may be to a large degree removed during the warm-up period as described above to provide a high concentration of steam therein. Alternatively, however, at least a portion of the air may be removed from the interior chamber 20 by using a vacuum pump or other suitable device for removing the air or other fluid in the interior chamber prior to the introduction of saturated steam from the steam generator 42. Such evacuation of the initial contents of the interior chamber 20 may decrease the warm-up period for establishing a high concentration of steam at the desired operational temperature.

As described above, in one embodiment, the temperature of the superheated steam within the interior chamber 20 may be maintained at the desired operational temperature during the entire sterilization period. For example, such an embodiment is illustrated by line A in FIG. 3. In another embodiment, however, thermal cycling may be used during the sterilization period. Such an embodiment is illustrated by line B in FIG. 3. In this embodiment, at some point prior to or during the sterilization period, the flow of saturated steam from steam generator 42 is turned off. This may occur, for example, after the steam in interior chamber 20 has reached the desired concentration of steam (e.g., 85% or higher). The heater 64 in the recirculation loop 54 is then turned off so that the temperature of the steam in the interior chamber 20 falls from the operational temperature ($T_o$) to below the saturation temperature ($T_s$) of the steam, which at one atmosphere is approximately 100° C. The temperature may be dropped to a temperature below the saturation temperature ($T_s$) so that condensation begins to form in the interior chamber 20, this temperature may be referred to as a condensation temperature ($T_c$). For example, the temperature may be dropped to approximately 80° C. when steam is the working fluid. However, temperatures from about 20° C. to 100° C. are anticipated for normal room temperature placement of the sterilizing apparatus 10. Those of ordinary skill in the art will recognize that other temperatures are also possible so as to allow the steam to start condensing.

Figure 3:
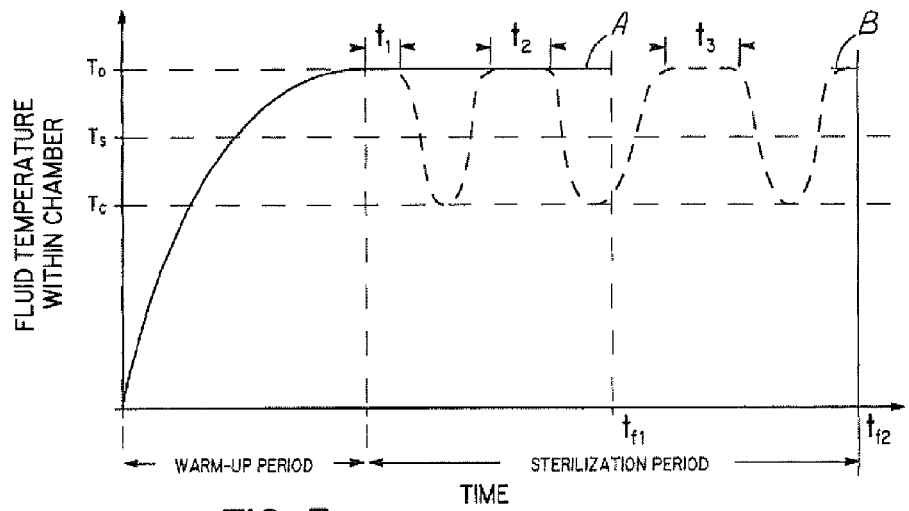
FIG. 3 is a graph illustrating operation of the sterilizing apparatus including thermal cycling.

When the temperature reaches the condensation temperature ($T_a$), the heater 64 may be re-energized so as to start heating the steam again and bring the steam back above the saturation temperature ($T_s$) and to the operational temperature ($T_o$). The temperature may be held at the operational temperature ($T_o$) for a certain period of time and then the cycle repeated. Thus, multiple thermal cycles may be initiated during the sterilization period, as shown in FIG. 3. While FIG. 3 shows three such thermal cycles, more or less cycles may be initiated depending on the specific application. While perhaps not fully understood, it is believed that thermal cycling during the sterilization period facilitates penetration of the steam into the items being sterilized or their packages. As is generally known in the art, for effective sterilization, the steam must penetrate the pouches in which the items are contained. Additionally, once within the pouches, the steam may have to penetrate several layers of linens (due to folding or configuration of items within the interior chamber) so as to sterilize the full extent of the item. The ability to penetrate the various items being sterilized is thus important and it is believed that thermal cycling enhances the penetration of steam and thus the sterilization process as a whole. While some form of thermal cycling has been used in various autoclave sterilization processes, such thermal cycling is achieved by pressure cycling the chamber, the pressure then controlling the temperature to produce a resulting thermal cycle. However, pressure cycling to achieve the desired thermal cycling requires various pumps, valves, regulator, etc. which undesirably add to the cost, size, etc. of the autoclave. In the sterilizing apparatus 10 as described above, the temperature and the pressure of the fluid in the interior chamber 20 are effectively substantially decoupled from each other (unlike in autoclaves). Accordingly, thermal cycling of the fluid in the interior chamber 20 may be relatively easily achieved by simply controlling the heater 64, such as by turning the heater 64 on and off, or alternatively, controlling the heater 64 in a manner that achieves the desired thermal cycling.

Those of ordinary skill in the art will recognize that the time that the interior chamber 20 is held at the operational temperature ($T_o$) between cycles may be varied as desired or as dictated by the specific application. For example, times t.sub.1, $t_2$, and $t_3$ in FIG. 3 may all be equal or be different from each other. In addition, the time it takes the steam within the interior chamber 20 to be brought down to the condensation temperature ($T_c$) may also be varied and/or controlled. For example, at one end of the time spectrum, the heater 64 may be simply turned off and the steam in interior chamber 20 permitted to cool due to natural or unaided heat transfer away from enclosure 18. This cooling time, however, may be reduced by actively facilitating heat transfer away from enclosure 18. Thus, in one alternative embodiment, a cold fluid, such as air or water, may be circulated over enclosure 18 to more quickly reduce the temperature of the steam located within interior chamber 20. Alternatively, a heat exchanger 68 (e.g., refrigerator, chiller, etc.), shown in phantom in FIG. 2, may be in thermal communication with the steam flowing through recirculation loop 54 so as to cool the steam in interior chamber 20. Other alternatives may also be possible as recognized by those of ordinary skill in the art.

Figure 4:
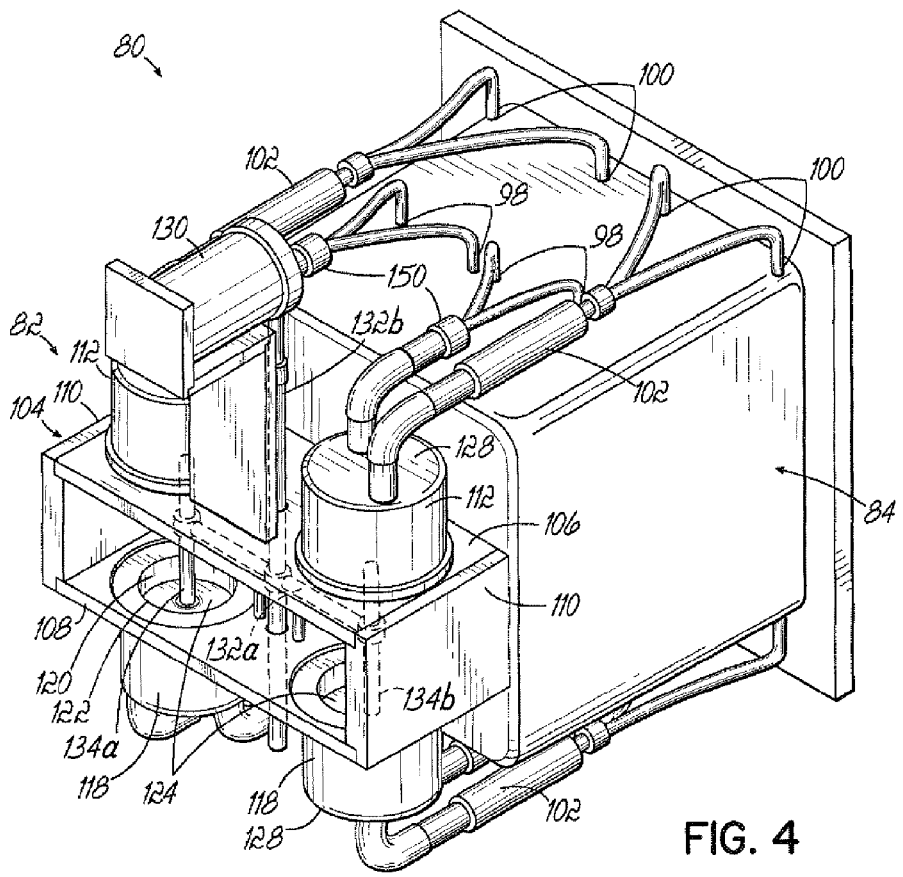
FIG. 4 is a perspective view of a sterilizing apparatus in accordance with a second embodiment of the invention.

As noted above, in order to allow the fluid in the interior chamber 20 to consist of a high percentage of steam, it is important that the enclosure 18, including the recirculation loop 54, be fluid tight so that no air or other environmental gases leak into the interior chamber 20. One source of leaks into the system may be the pump 62 used to circulate the fluid in interior chamber 20 through recirculation loop 54 and through heater 64 to, in essence, superheat the steam. While fluid tight rotary-type pumps are available and may operate for its intended purpose as described above, such pumps may be cost prohibitive and difficult to maintain. Accordingly, it may be desirable to use a different type of pump that provides a fluid tight seal and which is more reliable and cost effective. To this end, a sterilizing apparatus 80 is shown in FIG. 4 that utilizes a pump 82 that provides a more reliable fluid tight seal and that is cost effective. The sterilizing apparatus 80 is similar to sterilizing apparatus 10 described above and may operate in a manner similar to sterilizing apparatus 10, including all the alternatives described above. Accordingly, modifications to sterilizing apparatus 80 relative to sterilizing apparatus 10 will primarily be described herein. To facilitate this discussion, a diagram similar to FIG. 2, is shown in FIG. 5.

Sterilizing apparatus 80 includes an enclosure 84 defining an interior chamber 86 and a door (not shown) for selectively accessing the interior chamber 86. Although not shown, the enclosure 84 may be incorporated into a cabinet similar to cabinet 12 shown in FIG. 1 or incorporated into another type of frame or supporting structure for supporting the enclosure 84 on the floor, table, or other surface. The enclosure 84 may have a double-walled construction that effectively reduces heat loss from the enclosure 84 so as to, in essence, provide an insulation layer about is outer bounds, as discussed above. The sterilizing apparatus 80 includes a steam generator 88 (not shown in FIG. 4) similar to steam generator 42 in fluid communication with interior chamber 86 for introducing saturated steam therein. Sterilizing apparatus 80 also includes a one-way valve 92 that provides a fluid communication path between the interior chamber 86 and the surrounding environment 94. As described above in reference to valve 50, the one-way valve 92 operates as a vent to allow slightly pressurized fluid within interior chamber 86 (e.g., air, steam, air-steam mixture, etc.) to flow out of the interior chamber 86, but prevents air or other environmental gases, fluids, etc. to flow into the interior chamber 86 through the valve 92.

Figure 5:
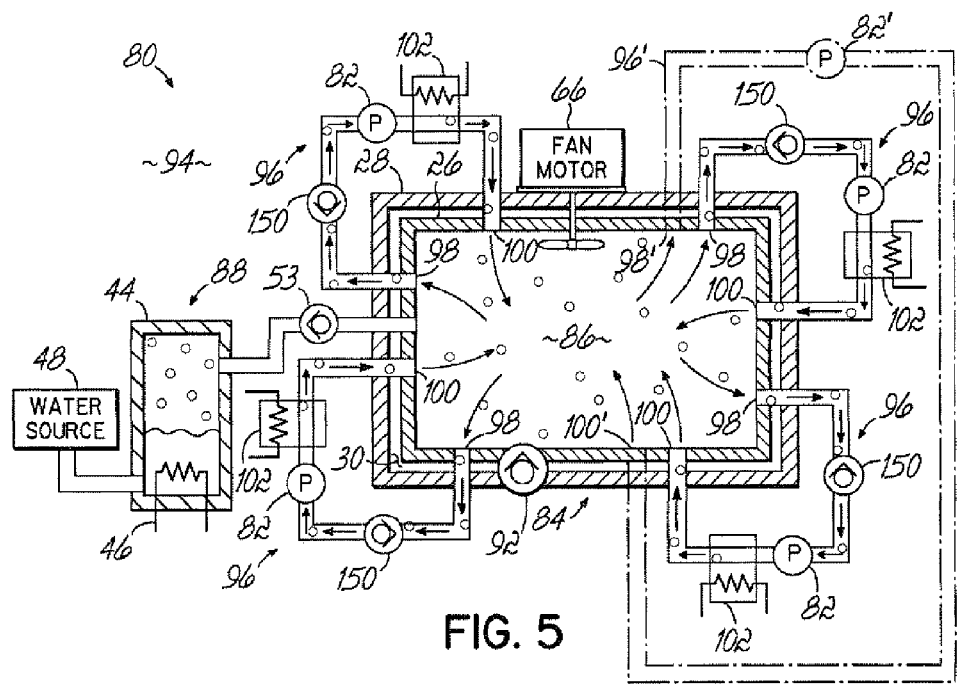
FIG. 5 is a diagrammatic illustration of the sterilizing apparatus shown in FIG. 4.

As noted in the diagram in FIG. 5, the sterilizing apparatus 80 includes a plurality of recirculation loops 96, each having one or more inlets 98 in fluid communication with the interior chamber 86, and one or more exits 100 also in fluid communication with interior chamber 86. For each recirculation loop 96, fluid from within the interior chamber 86 flows through the inlet(s) 98, through the recirculation loop 96, and back into the interior chamber 86 through the exit(s) 100. To promote such a flow through the recirculation loops 96, each loop may include a pump 82, as will be discussed in more detail below. Each recirculation loop 96 may further include a heater 102 for heating the saturated steam from steam generator 88 to produce superheated steam within interior chamber 86. As described above, the heater 102 may be the heater disclosed in U.S. Publication No. 2007/0145038, PCT application Ser. No. PCT/US07/84670, entitled "Heating and Sterilizing Apparatus and Method of Using Same" filed on Nov. 14, 2007, or another type of heater for effectively heating the fluid in the recirculation loops 96.

Figure 6:
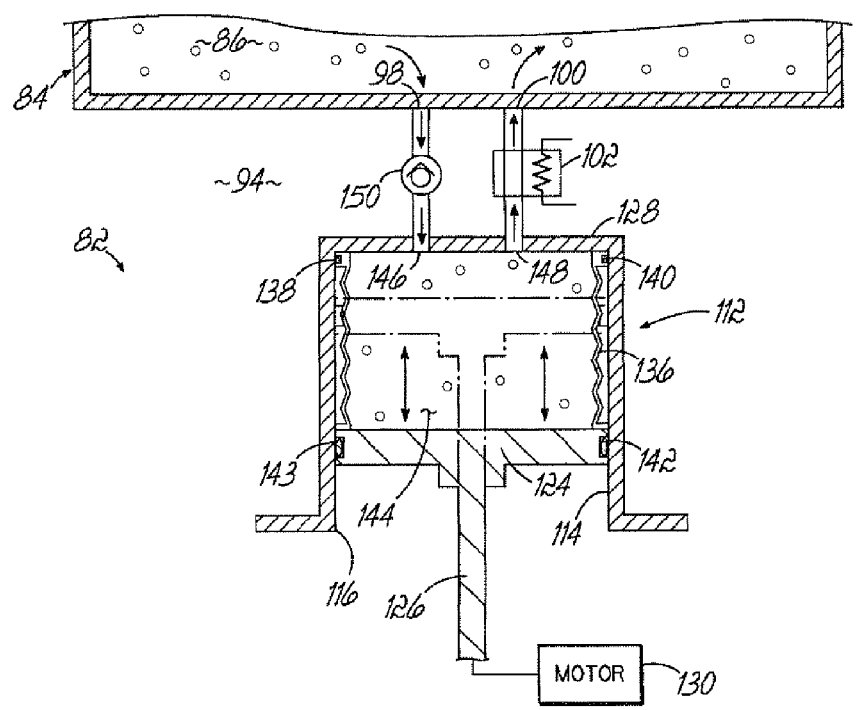
FIG. 6 illustrates a bellows pump in accordance with an embodiment of the invention.

In this embodiment, and as shown in FIGS. 4 and 6, the pump 82 may be a bellows-type of pump that overcomes many of the sealing issues associated with rotary type of pumps. In this regard, and in one embodiment, the enclosure 84 includes a pump housing 104 coupled thereto having a top wall 106, a bottom wall 108, and a pair of side walls 110. The top wall 106 includes a pair of spaced cylindrical sub-housings 112 extending therefrom and defining blind bores 114 having openings 116 in communication with an interior of pump housing 104. The bottom wall 106 likewise includes a pair of spaced cylindrical sub-housings 118 extending therefrom and defining blind bores 120 having openings 122 in communication with an interior of pump housing 104. In one embodiment, the sub-housings 112 vertically align with sub-housings 118, as illustrated in FIG. 4. A piston 124 may be movably disposed in each of the bores 114, 120 and configured for reciprocating movement therein. A piston rod 126 may be coupled to each piston 124 for moving the piston between a first position and a second position within the bores 114, 120. When in the first position, the pistons 124 may be adjacent to an end wall 128 of the bores 114, 120 opposite the respective openings 116, 122. In the second position, the pistons 124 have been moved away from the end wall 128 and toward the openings 116, 122. The movement of the pistons 124 may be due to a motor 130 operatively coupled to the pistons 124 via one or more drive shafts 132, which are in turn operatively coupled to the pistons rods 126. The motor 130 may include any number of gears, rack, pinions, cams, etc. for converting the rotary motion of the motor 130 into linear movement of the drive shafts 132. Those of ordinary skill in the art will recognize other types of devices capable of producing linear, rotary, or other movement for actuating the pistons 124 between the first and second positions.

As illustrated in FIG. 4, the pump 82 may have a tandem design. In this design, the piston rods 126 extending from the pistons 124 in aligned sub-housings 112, 118 are coupled to each other. In one embodiment, the piston rods 126 may be integrated into a single, unitary rod 134a, b. A first drive shaft 132*a* then rigidly couples the two unitary rods 134*a, b* with a second drive shaft 132*b* operatively coupled to motor 130 to drive the unitary rods 134*a, b* in tandem. Thus, when the pistons 124 in sub-housing 112 are in the first position, the pistons 124 in sub-housing 118 are in the second position. In a similar manner, when the pistons 124 in sub-housing 112 are in the second position, the pistons 124 in sub-housing 118 are in the first position. Those of ordinary skill in the art will recognize that the tandem design as described above is exemplary and other designs are also possible. For example, each sub-housing may have a dedicated motor for moving the pistons between the first and second positions. Alternatively, a single motor may move each of the pistons between the first and second positions in unison. Other designs are also possible as recognized by those of ordinary skill in the art.

As illustrated in FIG. 6, the sealing of the pump 82 from the surrounding environment 94 may be achieved with an elongated bellows seal, generally shown at 136, disposed in each of the sub-housings 112, 118. Each bellows seal 136 includes a first end portion 138 sealingly coupled to the sub-housings 112, 118 adjacent the end wall 128, such as at 140. Each bellow seal 136 also includes a second end portion 142 sealingly coupled to the periphery of the piston 124, such as at 143. The bellows seals 136 each define a bellows chamber 144 for receiving and expelling the fluid in the interior chamber 86 of enclosure 84. The bellows seal may be made out of any suitable material such as thin stainless steel, silicone, molded materials like rubber, and other commonly flexible, elastic or bendable materials. Operation of the pump 82 will not be described.

The operation of the sterilizing apparatus 80 is similar to that described above in reference to FIGS. 1 and 2. Accordingly, the following description will primarily focus on the operation of the pump 82. When the pump 82 is energized so as to initiate flow through the recirculation loops 96, motor 130, via drive shafts 132 and pistons rods 126, causes the pistons 124 to move between their first and second positions. For purposes of discussion, only one recirculation loop 96 as illustrated in FIG. 6 will be described. It is recognized, however, that the description also applies to the remaining recirculation loops 96. Moreover, for purposes of discussion, it will be assumed that the piston 124 is initially in the first position (shown in phantom in FIG. 6). As the piston 124 is moved from the first position and toward the second position, the bellows chamber 144 expands, thus creating a vacuum that effectively draws fluid within interior chamber 86 through the inlet(s) 98, into the recirculation loop 96, and through an inlet port 146 in end wall 128 in fluid communication with the bellows chamber 144. Fluid from the interior chamber 86 will flow into the recirculation loop 96 until the piston 124 reaches the second position (shown in solid in FIG. 6). The movement of the piston 124 now changes direction such that the piston 124 moves from the second position toward the first position. This movement collapses the bellows chamber 144 so as to pressurize the fluid therein and cause the fluid to flow through an exit port 148 in fluid communication with bellows chamber 144, through the heater 102 in the remaining portion of circulation loop 96, and back into the interior chamber 86 through exit(s) 100. The repeated expansion and collapse of bellows chamber 144 then provides a pulsed flow of fluid through the recirculation loop 96. As before, however, the fluid in the interior chamber 86 eventually reaches a high concentration of steam at the desired operational temperature. Sealing the interior chamber 86 (including recirculation loop 96) from the environment 94 using the bellows pump 82, however, may be less problematic and more cost effective as compared to other pump designs to achieve such high concentrations of steam within interior chamber 20.

In an alternative embodiment (not shown), the bellows chamber 144 may be defined between the external surface of the bellows seal 136 and the interior of the sub-housing 112 (e.g., external to the bellows seal 136) with the inlet and exit ports 146, 148 positioned so as to be in fluid communication with the bellows chamber 144. Such an embodiment would require the housing 112 to form a portion of the bellows chamber 144. However, in an alternative embodiment to that shown in FIG. 6, the housing 112 may be eliminated (e.g., one end of the bellows 136 may be attached directly to the enclosure 84 and the bellows chamber 144 would be defined internally of the bellows seal 136 without the support of the housing 112.

In another alternative to that described above, during the flow/pulsing of the bellows chamber 144, i.e., movement of the piston 124 from the second position and toward the first position, it may be possible for some of the fluid contained therein to flow back through the inlet port 146 and into the interior chamber 86 thus bypassing the heater 102. To prevent such an occurrence, the recirculation loop 96 may include a one-way valve 150 (e.g., check valve) that allows fluid to flow from the interior chamber 86 toward the bellows chamber 144, but prevent fluid to flow from the bellows chamber 144 toward the interior chamber via inlet port 146. The one-way valve 150 may be similar to that described above for valve 50. In this way, when the bellows chamber 144 is compressed, the fluid contained therein flows through the exit port 148 so as to be heated by heater 102 prior to being returned to the interior chamber 86. Such a configuration provides more efficient heating and operation of the recirculation loop 96. Furthermore, ensuring that the fluid passes through heater 102 before returning to interior chamber 186 provides in effect, a fluid path for eliminating prions and other very hardy microorganisms, which require high heat and high temperatures for destruction thereof. In this way, mixed or individual microorganisms such as mixtures of prions and bacteria, and even viruses are removed because the fluid can independently pass through a very high heat region (i.e., the heater 102) without necessarily subjecting the interior chamber 86 itself to such high heat and temperatures as is sometimes required for denaturing prions, viruses and other hardy microorganisms. Furthermore, although not shown, a one-way valve may also be associated with exit port 148 so that no fluid may return to the bellows chamber 144 after having passed through heater 102.

There are also a number of modifications that may be made to the sterilizing apparatus 80 within the scope of the invention. By way of example, the number of inlet(s) 98 and exit(s) 100 may be configured to meet a specific application. As noted before, an outlet 100 may be positioned at the midpoint of each of the walls of the enclosure 84 so as to provide a more uniform distribution of superheated steam within interior chamber 86. As discussed above, the air in interior chamber 86 may be partially or fully evacuated therefrom prior to introducing steam from steam generator 88 so as to decrease the warm-up period of the sterilizing apparatus 80. Thermal cycling may also be used in the operation of sterilizing apparatus 80 to facilitate penetration of superheated steam into items being sterilized in the manner as described above.

In addition, one or more recirculation fans 66 may be used to further ensure a uniform distribution of steam within interior chamber 86. In an alternative embodiment, instead of, or in addition to, recirculation fan(s) 66, a pulsating bellows may be used to effectively stir the fluid in the interior chamber 86. To this end, and as shown in phantom in FIG. 5, a recirculation loop 96' may include one or more inlets 98', one or more exits 100' and a bellows pump 82' for pulsing the flow through the recirculation loop 96'. The bellows pump 82' may be similar in construction and operation to pump 82. However, as the flow rates through recirculation loop 96' may be lower than through recirculation loop 96, the pump 82' (sub-housing, piston, bellows chamber, etc.) may be smaller in size. In operation, the bellows pump 82' may be pulsed at a frequency of between approximately 1 pulse/sec to approximately 100 pulses/sec. Although the pulsing of the fluid in the interior chamber 20 may be achieved by one or more dedicated recirculation loop 96'. It should be recognized that the recirculation loops 96 may be modified to achieve the pulsing of the flow, such as by the inclusion of the pump 82' in one or more of the loops 96 illustrated in FIG. 5. It should further be recognized that the pumps 82 themselves may be modified to achieve the pulsing by adding a small-amplitude, high frequency pulse to the bulk motion of the pistons 124. Other ways may also be possible as recognized by those of ordinary skill in the art.

The sterilizing apparatus as described above provide a number of advantages over existing devices that provide sterile items, including existing autoclaves. For example, one aspect of the invention is that the sterilizing apparatus provides superheated steam at substantially one atmosphere of pressure. This is in stark contrast to autoclaves that use increased pressure to produce superheated steam at a desired temperature (e.g., 121° C. or 134° C.). Accordingly, the sterilizing apparatus in accordance with aspects of the invention are not required to meet various federal and state regulations on pressure vessels, and the enclosures that define the internal chambers may be less bulky and lighter in weight. Furthermore, because pressure is not used to generate the superheated steam, the sterilizing apparatus in accordance with the invention uses significantly less steam. Accordingly, smaller and lighter localized steam generators may be used to supply the saturated steam to the interior chamber. This overcomes the heavy, bulky localized steam generators typically used in autoclaving. Such a result may also obviate the need for any remote steam generation. In other words, even for relatively large sterilizing apparatus in accordance with embodiments of the invention, localized steam generators may be capable of generating the necessary steam. Thus, the sterilizing apparatus are more mobile and versatile and are not restricted to being placed adjacent a dedicated steam port. Additionally, the smaller, lighter steam generators used in sterilizing apparatus as described herein may provide a reduced machine footprint so as to conserve floor, countertop, or tabletop space. Furthermore, because less steam has to be produced, the steam generators may be more energy efficient.

The sterilizing apparatus in accordance with embodiments of the invention are also more robust as compared to existing autoclaves. By way of example, and in reference to FIG. 7, which is a diagrammatic illustration, a sterilizing apparatus 160 in accordance with aspects of the invention may be configured to operate in different modes corresponding to different types of sterilization. Sterilizing apparatus 160 is similar to sterilizing apparatus 10 and like reference numerals refer to like features in FIGS. 1 and 2. In this embodiment, however, a multi-positional valve 162 may be configured such that when valve 162 is in a first position, saturated steam from steam generator 42 flows into interior chamber 20. Thus, the sterilizing apparatus 160 may operate in a wet heat sterilization mode, which is described above. The sterilizing apparatus 160 may also operate in a dry heat sterilization mode when the valve 162 is in a second position. When the valve 162 is in the second position, a dry gas source 164 may be in fluid communication with the interior chamber 20 for supplying a dry gas, such as air, nitrogen, carbon dioxide, other noble gases, carbon containing gases, or chlorides, bromides, etc.

In this dry heat sterilization mode, the sterilizing apparatus 160 operates in a similar manner as described above. Thus, a mixture of gases might initially exist in the interior chamber 20. The pump 62 and heater 64 are energized to initiate a flow of the gas mixture through the recirculation loop 54, wherein the mixture is heated. As the gas mixture becomes heated, the pressure slightly starts to increase within the interior chamber 20. Consequently, the one-way valve 50 opens and vents the gas mixture from the interior chamber 20. Because the enclosure 18 and recirculation loop 54 are fluid-tight, i.e., no air or other fluid from the surrounding environment 52 may enter the sterilizing apparatus 10 after the door is closed, and because only 100% dry gas is introduced into the interior chamber 20 from dry gas source 164, the percentage of dry gas in the interior chamber 20 steadily increases from essentially zero and toward 100% over a certain period of time and at approximately atmospheric pressure, due to the venting through the one-way valve 50. The fluid in the interior chamber 20 may have a high concentration of the dry gas (including 100% dry gas). In addition, because the gas mixture flows through the recirculation loop 54 and heater 64, the gas eventually reaches the desired operating temperature of the sterilizing apparatus 160. Thus, for example, the dry gas that eventually fills the interior chamber 20 may reach a temperature of 160° C., 180° C., or higher temperatures, as dictated by the specific application. The interior chamber 20 may be maintained at this temperature and pressure for a specified amount of time depending on the particular application. This time may be determined so that the bacteria, viruses, spores, prions, and other microorganisms on the items located in the sterilizing apparatus 10 are destroyed through the dry heat sterilization process. This time may be determined by various federal or state regulations, health codes, etc. or otherwise determined as recognized by those of ordinary skill in the art. Similar to above, less than pure dry gas may be introduced into interior chamber 20 such that the maximum concentration of the dry gas achieved in the interior chamber is less than 100%.

Figure 7:
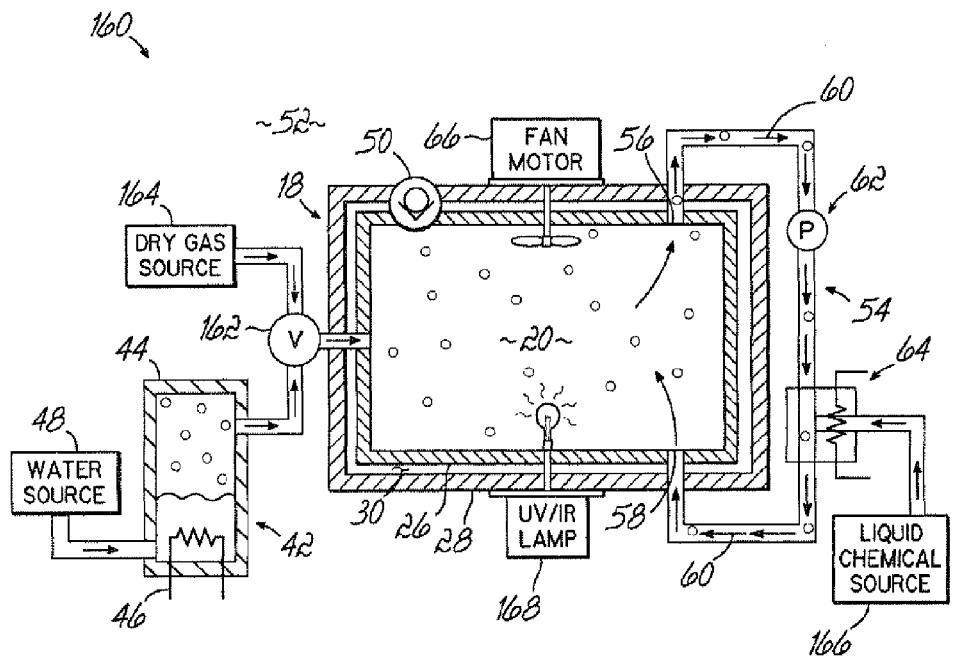
FIG. 7 is a diagrammatic illustration of the sterilizing apparatus in accordance with a further embodiment of the invention.

Sterilizing apparatus in accordance with aspects of the invention may also use a chemical mode of sterilization. In one embodiment, for example, a liquid or gaseous chemical may be introduced into the interior chamber 20 to complement the sterilization achieved by the wet or dry heat sterilization as described above. More particularly, a superheated chemical may be introduced into the interior chamber 20 via the heater 64 as more fully disclosed in U.S. Publication No. 2007/0145038 or PCT application Ser. No. PCT/US07/84670, entitled "Heating and Sterilizing Apparatus and Method of Using Same" filed on Nov. 14, 2007. In reference to FIG. 7 of this publication, the heater may include a reservoir for containing a liquid, such as a liquid chemical effective for sterilization. Through a venturi effect, the liquid may be pulled into a bulbous reactor vessel where it mixes with a heated gas stream (e.g., superheated steam or dry gas) to vaporize the liquid chemical. As illustrated in FIG. 7 of the present application, a liquid chemical source 166 may be in fluid communication with the heater. The liquid chemical may be vaporized and mixed with the fluid flowing through recirculation loop 54. This mixture is then circulated through the interior chamber 20 as described previously. Such a multi-mode sterilization process may produce a synergistic effect for sterilizing the items located within the interior chamber 20.

It should be realized that sterilizing apparatus in accordance with embodiments of the invention are not limited to the use of water as the working fluid. To this end, and in reference to FIG. 2, the water source 48 may be replaced with an alternative fluid source (not shown). For example, the fluid source may include paracetic acid, formaldehyde, propyleneoxide, hydrogen peroxide, glutaraldehyde, pesticides, and sodium compounds like benzanates, alcohol, disinfectants, bleach, etc. Various wound healing fluids, like non-alcohol based Dermacyn®, may be used with the apparatus, either alone or in combination with the steam. In this regard, such non-alcohol fluids will not ignite, even when used at very high temperatures. Operation of the sterilizing apparatus with the alternative fluid source is similar to that described above in reference to FIG. 2 and the use of water as the working fluid. In addition, the sterilizing apparatus in accordance with aspects of the invention may be used in conjunction with various forms of radiation to achieve additional sterilization of items located within interior chamber 20. For example, a UV, IR, or RF source 168 may be positioned within interior chamber 20 so as to expose the items for sterilization to UV, IR, or RF radiation that facilitates the destruction of microorganisms on the items positioned therein. Such UV/IR light sources are commercially available from Philips Electronics, for example. The interior chamber 20 may also be modified to use other forms of radiation including x-rays, gamma rays, microwaves, etc. Ultrasound may also be used within interior chamber 20.

As demonstrated from the above, sterilizing apparatus in accordance with embodiments of the invention may be a single apparatus capable of operating in different modes, e.g., wet heat sterilization, dry heat sterilization, chemical sterilization, radiation, and combinations thereof. Accordingly, different apparatus do not have to be purchased for the different kinds of sterilization. This may results in significant cost savings for those that use or desire to use different modes of sterilization. It should be recognized that the modifications of the sterilizing apparatus 10 as illustrated in FIG. 2 so as to arrive at sterilizing apparatus 160 illustrated in FIG. 7 may also be made to sterilizing apparatus 80 illustrated in FIG. 5.

As noted above, one of the more serious flaws in autoclaves is that they operate at selected temperatures (e.g., 121° C. or 134° C.) and are not capable of operating at variable and increased temperatures. Such a drawback is overcome by the sterilizing apparatus in accordance with embodiments of the invention. In the embodiments described above, the temperature of the fluid in the interior chamber 20, 86 are primarily dictated by the heater(s) 64, 102. Thus, increasing the power to heater(s) 64, 102 will result in a corresponding increase in the temperature of the fluid in interior chamber 20, 86. Although not shown, the heater(s) 64, 102 may be coupled to a central controller for controlling the heat generated thereby. Additionally, one or more temperature-sensing devices, such as a RTD, thermocouple, or other such device, may be positioned within the interior chamber 20, 86 and operatively coupled to the controller so as to provide a feed-back system that adjusts the heater(s) 64, 102 to maintain a specified temperature within the interior chamber 20, 86. The controller may use wireless technology to control the heater(s) 64, 102 and/or to report the status of the sterilizing apparatus to a remote location. Depending on the type of heaters 64, 102, a wide range of operating temperatures is available. For example, a heater 64, 102 in accordance with that disclosed in U.S. Publication No. 2007/0145038 or PCT application Ser. No. PCT/US07/84670, entitled "Heating and Sterilizing Apparatus and Method of Using Same" filed on Nov. 14, 2007 may provide a superheated gas as high as 1,500° C. Unlike autoclaves, sterilizing apparatus in accordance with embodiments of the invention may achieve these high temperatures at approximately one atmosphere of pressure. Accordingly, if the federal, state, and/or local health standards or regulations change so as to require an increased temperature for sterilizing various items, the sterilizing apparatus as described herein may be easily configured to meet such standards or regulations. It is anticipated that as microorganisms mutate, evolve, etc., higher temperatures will be required to destroy such microorganisms. While the sterilizing apparatus as described above may accommodate such changes, autoclaves will most likely have to be completely replaced as the ability to modify existing autoclaves for higher pressures so as to produce higher temperatures is problematic, if possible at all. Such a wholesale replacement would be cost prohibitive, especially to smaller business and offices. However, it may be possible to modify existing autoclaves so as to operate in a manner similar to that described above for the sterilizing apparatus 10, 80, 160. Thus, in another embodiment in accordance with the invention, a retrofit kit (not shown) may be provided which will allow the autoclave to generate superheated steam using a heater and valving as described above as opposed to using increased pressures. By way of example, an autoclave may be modified to include a recirculation loop which is in fluid communication with the autoclave chamber. The recirculation loop may include the one-way valve, pump, and heater so as to generate a high concentration of superheated steam in the manner described above.

Various embodiments of the sterilizing apparatus 10, 80, 160 according to aspects of the invention were tested and the results are presented herein.

Example 1

An experiment to determine the efficacy of a sterilizing apparatus built in accordance with that illustrated in FIGS. 1 and 2 to kill the bacteria enterobacter aerogenes was conducted. In this experiment, the bacteria, which was suspended in a liquid media, was swabbed onto a surface of two stainless steel coupons (20 mm×30 mm×2 mm) and allowed to stand for about fifteen minutes. One of the coupons was then inserted into the sterilizing apparatus and subjected to superheated steam at an operational temperature of 130° C. for a period of forty-five minutes. After the sterilizing cycle, a swab was taken off of the treated coupon and transferred into a nutrient media and stirred for about one minute. For example, Easygel® kits from Micrologylabs may be used in this capacity. The gel nutrients were then transferred into a Petri dish supplied with the kits. The same steps were then taken for the control coupon (i.e., non-treated coupon). The Petri dishes were then incubated at 85° C.+/−5° F. for about forty hours. After the incubation period, the Petri dishes were visually observed for any growth of the bacteria, which would be indicated by red dots or regions within the Petri dish media. The treated sample indicated no red dots/regions. The control sample, however, indicated many red dots/regions, and thus the presence of the bacteria enterobacter aerogenes. Accordingly, it is believed that the sterilizing apparatus was effective for killing or destroying the bacteria enterobacter aerogenes.

Example 2

A similar experiment as that described above was then conducted on the bacillus cereus bacteria. The same process as that described above was used. Again, the treated sample indicated no red dots/regions (colonies of bacterial growth) while the control sample indicated many red dots/regions and thus the presence of the bacillus cereus bacteria. Accordingly, it is believed that the sterilizing apparatus was effective for killing or destroying the bacteria bacillus cereus.

Example 3

An experiment to determine the efficacy of a sterilizing apparatus similar to that illustrated in FIG. 1 or FIG. 7 to kill bacteria using dry heat sterilization was conducted. In this experiment, a biological indicator (bio-indicator) for steam sterilizers/autoclaves was used to determine the efficacy of the sterilization apparatus. Bio-indicators are well known in the art and also commercially available from, for example, SGM Biotech, Inc, or other vendors. In general, bio-indicators include a first compartment containing microbial spores (e.g., *geobaccillus stearothermophilus*) and a second compartment with a growth medium and growth indicator. At the conclusion of a sterilizing procedure, the barrier between the two compartments is broken so that the growth medium/indicator mixes with the spores. The bio-indicator is then incubated for a period of time to allow the growth of the bacteria if present (e.g., between 15-48 hours or higher, wherein the recommended time from the manufacturer is 24 hours). If the sterilization procedure killed the spores, then the medium will remain its initial color (e.g., purple). If, on the other hand, the sterilization procedure was unsuccessful, the spores will metabolize/grow and cause the medium to turn to a second color (e.g., yellow). In this experiment one dry heat bio-indicator was inserted into the sterilization apparatus and subjected to air at 180° C. for a period of ninety minutes. Another dry heat bio-indicator was used as a control sample. After the sterilization procedure, the barrier between the compartments were broken and the bio-indicators incubated for a period of fifteen hours at a temperature of about 90° F. The treated bio-indicator remained its initial purple color. The control bio-indicator, however, turned yellow, thus indicating the presence of the bacteria. Accordingly, it is believed that the sterilizing apparatus using dry heat sterilization was effective for killing or destroying the spores in the bio-indicator.

While the sterilizing apparatus in accordance with the embodiment illustrated in FIGS. 1 and 2 is believed to be effective for destroying microorganisms, as supported by the experiments provided above, it was believed that the sterilizing apparatus in accordance with that illustrated in FIGS. 1 and 2 and using steam as the working fluid may not be capable of passing the more stringent testing requirements mandated for the autoclave industry (e.g, steam labels, bio-indicators, Bowie-Dick test) in an apparatus which may not be completely sealed. The primary reason for this is that it is believed that to pass the testing requirements for the autoclave industry, a very high concentration of steam must be used within the chamber. To reach these high concentrations of steam, it may be important that the recirculation loop(s) be fluid tight so as to prevent any air or other environmental fluids from leaking into the chamber.

As the sterilizing apparatus built in accordance with that illustrated in FIGS. 1 and 2 used conventional pumps (rotary types with shafts, bearings, etc.), preventing leaks into the chamber, and thus the ability to attain high concentrations of steam, was considered problematic. This realization was a motivation for the development of the sterilizing apparatus illustrated in FIGS. 4-6, which used a bellows pump to provide the fluid flow through the heater. It was believed that the bellows pump design would provide a more reliable fluid tight (i.e., fully sealed) recirculation loop and chamber and thus allow the concentration of steam within the chamber to reach values suitable for passing the more stringent tests for the autoclave industry.

Accordingly, a sterilizing apparatus in accordance with the embodiment illustrated in FIGS. 4-6 was built and a number of experiments were conducted to determine the efficacy of the sterilizing apparatus to effectively destroy various microorganisms using metrics typically used in the autoclave industry. In this regard, steam labels, bio-indicators, and Bowie-Dick test packs were used in testing the bellows pump sterilizing apparatus. Steam labels are well known in the art and are commercially available from vendors such as 3M or Barnstead/Harvey. In general, however, if the steam label turns dark (e.g., black), the concentration of steam in the chamber is sufficiently high for destroying microorganisms. Bowie-Dick test packs are well known in the art and are commercially available from vendors such as Medline Industries, Inc. and others. In general, the Bowie-Dick test packs include a closed (but not fluid tight) carton containing an indicator sheet embedded within a stack of sheets on either side of the indicator sheet. The Bowie-Dick test is intended to determine the removal of air from the chamber (e.g., high concentration of steam) and steam penetration capability. In general, if the indicator sheet (which may initially be blue, for example) turns uniformly black, then air has been sufficiently removed from the chamber and the tested device provides adequate steam penetration.

Example 4

In one experiment, five steam labels and one bio-indicator were positioned at different locations within the interior chamber of a sterilizing apparatus in accordance with that illustrated in FIGS. 4-6. The following sterilization cycle was implemented:
i) saturated steam at a flow rate of 19.81 ml/minute was introduced into the interior chamber from a steam generator and the temperature of the steam in the interior chamber was brought from room temperature up to an operational temperature of 130° C. in 17 minutes;
ii) the temperature of the fluid in the interior chamber was maintained at 130° C. for six minutes;
iii) the temperature of the fluid in the interior chamber was decreased from 130° C. to 80° C. and back to 130° C. in an eighteen minute period. The steam generator was turned off when the temperature fell below about 100° C.;
iv) the temperature of the fluid in the interior chamber was maintained at 130° C. for forty-four minutes;
v) the temperature of the fluid in the interior chamber was decreased from 130° C. to 80° C. and back to 130° C. in a twenty-nine minute The steam generator was turned off when the temperature fell below about 100° C.;
vi) the temperature of the fluid in the interior chamber was maintained at 130° C. for sixty minutes;
vii) the temperature of the fluid in the interior chamber was decreased from 130° C. to 80° C. and back to 130° C. in a twenty minute period. The steam generator was turned off when the temperature fell below about 100° C.; and
viii) the temperature of the fluid in the interior chamber was maintained at 130° C. for sixty minutes.

The five steam labels all turned black indicating that the steam in the chamber was of sufficiently high concentration. Additionally, after the sterilizing procedure, the bio-indicator was activated (i.e., barrier between compartments broken) and incubated at 55° C.-60° C. for twenty-four hours. The bio-indicator did not turn yellow, thus indicating that the spores had effectively been destroyed in the sterilization process.

Example 5

An experiment similar to Example 4 described above was conducted but included only two thermal cycles (versus three in example 4). In this experiment, four steam labels were positioned at different locations within the interior chamber of a sterilizing apparatus in accordance with that illustrated in FIGS. 4-6. The following sterilization cycle was implemented:
  i) saturated steam at a flow rate of 22.2 ml/min was introduced into the interior chamber from a steam generator and the temperature of the steam in the interior chamber was brought from room temperature up to an operational temperature of 130° C. in 14 minutes;
  ii) the temperature of the fluid in the interior chamber was maintained at 130° C. for fifteen minutes;
  iii) the temperature of the fluid in the interior chamber was decreased from 130° C. to 80° C. and back to 130° C. in a twenty-two minute period with the steam generator off;
  iv) the temperature of the fluid in the interior chamber was maintained at 130° C. for sixty minutes;
  v) the temperature of the fluid in the interior chamber was decreased from 130° C. to 80° C. and back to 130° C. in a twenty-one minute period with the steam generator off; and
  vi) the temperature of the fluid in the interior chamber was maintained at 130° C. for sixty minutes;

The four steam labels all turned black indicating that the steam in the chamber was of sufficiently high concentration.

Example 6

In this experiment, steam labels, bio-indicators, and Bowie-Dick test packs were used with a sterilizing apparatus in accordance with that illustrated in FIGS. 4-6. In particular, a sealed sterilizing pouch was positioned on a bottom tray of the interior chamber and included a bio-indicator, a steam label, and stainless steel surgical scissors positioned therein. Such sterilizing pouches are conventional and are commercially available from vendors such as Henry Schein, Inc. of Melville, N.Y., and others. A Bowie-Dick test pack was positioned on a bottom tray near the door of the interior chamber. Three bio-indicators were also positioned on the bottom tray and five steam labels were variously positioned on both the top and bottom trays. Of the three bio-indicators on the bottom tray, two were immersed in distilled water prior to loading in the sterilizing apparatus, while one remained dry. The following sterilization cycle was implemented:
  i) saturated steam at a flow rate of 23.41 ml/minute was introduced into the interior chamber from a steam generator and the temperature of the steam in the interior chamber was brought from room temperature up to an operational temperature of 130° C. in fifteen minutes;
  ii) the temperature of the fluid in the interior chamber was maintained at 130° C. for eleven minutes;
  iii) the temperature of the fluid in the interior chamber was decreased from 130° C. to 80° C. and back to 130° C. in a thirty-nine minute period. The steam generator was turned off when the temperature fell below about 130° C.;
  iv) the temperature of the fluid in the interior chamber was maintained at 130° C. for sixty-nine minutes;
  v) the temperature of the fluid in the interior chamber was decreased from 130° C. to 80° C. and back to 130° C. in a sixty-nine minute period with the steam generator off;
  vi) the temperature of the fluid in the interior chamber was maintained at 130° C. for sixty-three minutes;
  vii) the temperature of the fluid in the interior chamber was decreased from 130° C. to 80° C. and back to 130° C. in a forty-three minute period with the steam generator off; and
  viii) the temperature of the fluid in the interior chamber was maintained at 130° C. for sixty-two minutes.

Figure 8:
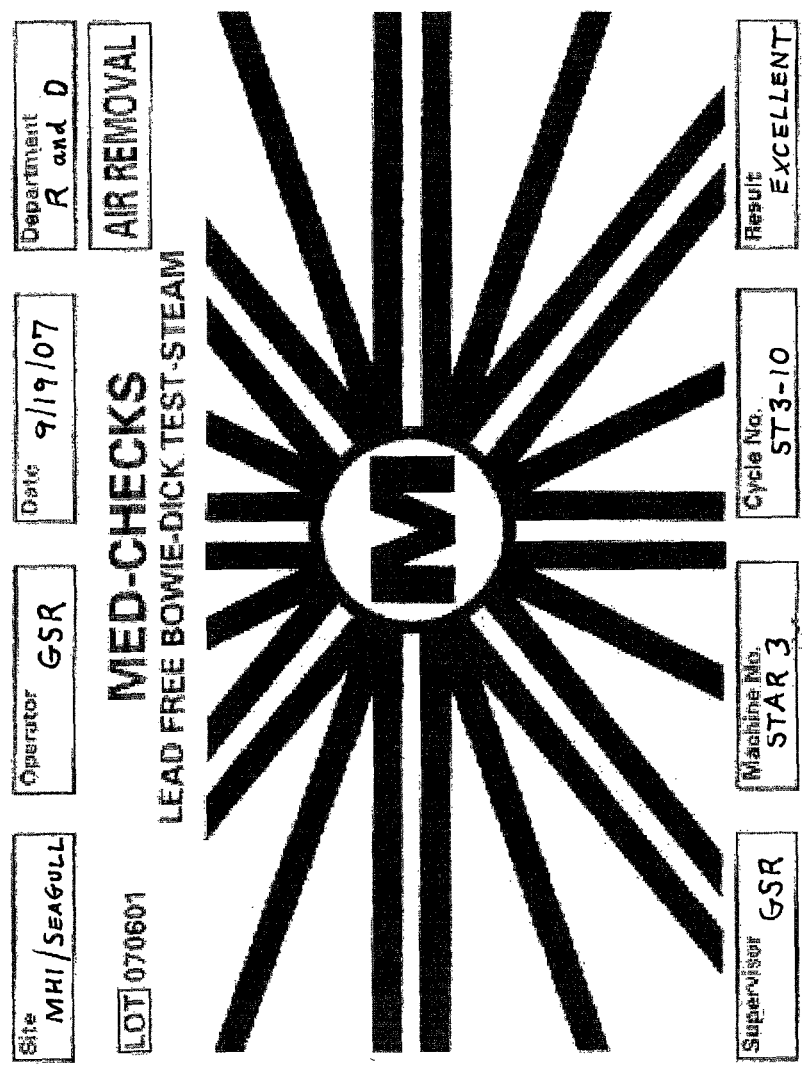
FIG. 8 illustrates the results of a Bowie-Dick test using a sterilizing apparatus in accordance with the invention.

The five steam labels positioned on the top and bottom trays all turned black indicating that the steam in the chamber was of sufficiently high concentration. Additionally, the steam label located in the sterilizing pouch also turned black indicating that the steam was capable of effectively penetrating such sterilizing pouches. In regard to the bio-indicators, after the sterilizing procedure, all four of the bio-indicator (including the bio-indicator in the pouch) were activated and incubated at 55° C.-60° C. for twenty-four hours. Upon inspection, none of the four bio-indicators turned yellow, thus indicating that the spores had effectively been destroyed in the sterilization process. In regard to the Bowie-Dick test, FIG. 8 shows the indicator sheet from the pack at the conclusion of the test. As illustrated, the indicator sheet turned completely and uniformly black, indicating that air had been sufficiently removed from the interior chamber and that the sterilizing apparatus provided adequate steam penetration.

Example 7

In another experiment, sixteen sterilizing pouches were placed on sixteen trays within the interior chamber of a sterilizing apparatus in accordance with that illustrated in FIGS. 4-6. Each of the sterilizing pouches included a surgical device, such as a surgical scissors, stainless steel forceps, or stainless steel flat pieces, and a steam label. Two of the sterilizing pouches included a bio-indicator. The following sterilization cycle was implemented:
  i) saturated steam at a flow rate of 18.1 ml/min was introduced into the interior chamber from a steam generator and the temperature of the steam in the interior chamber was brought from room temperature up to an operational temperature of 130° C. in twenty-two minutes;
  ii) the temperature of the fluid in the interior chamber was maintained at 130° C. for fifteen minutes;
  iii) the temperature of the fluid in the interior chamber was decreased from 130° C. to 80° C. and back to 130° C. in a fifty-one minute period with the steam generator off;
  iv) the temperature of the fluid in the interior chamber was maintained at 130° C. for sixty minutes;
  v) the temperature of the fluid in the interior chamber was decreased from 130° C. to 80° C. and hack to 130° C. in a sixty-nine minute period with the steam generator off;
  vi) the temperature of the fluid in the interior chamber was maintained at 130° C. for sixty minutes;
  vii) the temperature of the fluid in the interior chamber was decreased from 130° C. to 80° C. and back to 130° C. in a sixty-nine minute period with the steam generator off; and
  viii) the temperature of the fluid in the interior chamber was maintained at 130° C. for sixty minutes.

The sixteen steam labels located within the sterilizing pouches all turned black indicating that the steam in the chamber was of sufficiently high concentration and capable of penetrating the pouches. Moreover, after the sterilizing procedure, the two bio-indicators located in two of the sixteen pouches were activated and incubated at 55° C.-60° C. for twenty-four hours. Upon inspection, neither of the two bio-indicators turned yellow, thus indicating that the spores had effectively been destroyed in the sterilization process.

Example 8

In another experiment, a pack including a stainless steel basin with three folded surgical towels, gauze pads, and a thermocouple were wrapped in a surgical towel. Three steam indicators were located within the folds of a respective towel within the pack. The pack was then positioned with a sterilizing apparatus in accordance with that illustrated in FIGS. 4-6 in the form of a stack including nine folded surgical towels below the pack and three surgical towels on top of the pack. The following sterilization cycle was implemented:
  i) saturated steam at a flow rate of 13.1 ml/min was introduced into the interior chamber from a steam generator and the temperature of the steam in the interior chamber was brought from room temperature up to an operational temperature of 130° C. in fifty-eight minutes;
  ii) the temperature of the fluid in the interior chamber was maintained at 130° C. for seventeen minutes;
  iii) the temperature of the fluid in the interior chamber was decreased from 130° C. to 80° C. and back to 130° C. in an eighty minute period with the steam generator off;
  iv) the temperature of the fluid in the interior chamber was maintained at 130° C. for sixty minutes;
  v) the temperature of the fluid in the interior chamber was decreased from 130° C. to 80° C. and back to 130° C. in a twenty-eight minute period with the steam generator off;
  vi) the temperature of the fluid in the interior chamber was maintained at 130° C. for sixty minutes;
  vii) the temperature of the fluid in the interior chamber was decreased from 130° C. to 80° C. and back to 130° C. in a thirty-four minute period with the steam generator off; and
  viii) the temperature of the fluid in the interior chamber was maintained at 130° C. for sixty minutes.

The three steam labels located within the surgical towels in the pack all turned black indicating that the steam in the chamber was of sufficiently high concentration and capable of penetrating the surgical towels.

Example 9

In another experiment, five steam labels were positioned at different locations within the interior chamber of a sterilizing apparatus in accordance with that illustrated in FIGS. 4-6. The following sterilization cycle was implemented:
  i) saturated steam at a flow rate of 14.2 ml/min was introduced into the interior chamber from a steam generator and the temperature of the steam in the interior chamber was brought from room temperature up to an operational temperature of 130° C. in eighteen minutes;
  ii) the temperature of the fluid in the interior chamber was maintained at 130° C. for twenty-five minutes;
  iii) the temperature of the fluid in the interior chamber was decreased from 130° C. to 80° C. and back to 130° C. in a forty-seven minute period with the steam generator off;
  iv) the temperature of the fluid in the interior chamber was maintained at 130° C. for eighteen minutes;
  v) the temperature of the fluid in the interior chamber was decreased from 130° C. to 80° C. and back to 130° C. in a forty-five minute period with the steam generator off;
  vi) the temperature of the fluid in the interior chamber was maintained at 130° C. for twenty-one minutes;
  vii) the temperature of the fluid in the interior chamber was decreased from 130° C. to 80° C. and back to 130° C. in a forty-one minute period with the steam generator off; and
  viii) the temperature of the fluid in the interior chamber was maintained at 130° C. for eighteen minutes.

During the experiment, steam was observed coming out of one of the bellows indicating a leak in the system because a clamping mechanism had become slightly loosened. In any event, at the end of the cycle, the five steam labels had all turned black indicating that the steam in the chamber was of sufficiently high concentration.

The above description is not intended to limit the scope of the appended claims. Additional embodiments and modifications will readily appear to those skilled in the art. The aspects of the apparatus and methods described herein may be used for creating high wet heat and/or dry heat temperatures without the requirement of increased pressure. Additionally, aspects of the apparatus and methods described herein may be used in a manner to retrofit existing chambers, incubators, autoclaves, etc. in order to enhance their operation and performance. Such modifications may be helpful to treat new and emerging strains of bacteria and other microorganisms. Furthermore, aspects of the invention may be applied to larger scale applications. For example, the recirculation and concentration aspects may be incorporated into a venting system for a large chamber, such as a room, building, etc., for reducing or eliminating microorganisms in the air that flows into the room. It is anticipated that such an embodiment may be used to eliminate anthrax and other harmful agents from a space. Accordingly, departures may be made from such details without departing from the spirit and scope of applicants' inventive concept.

What is claimed is:

1. A method of sterilizing at least one item, comprising: introducing a first working fluid into an interior chamber having an inner wall; holding the item to be sterilized; circulating the first working fluid in the interior chamber through at least one fluid tight recirculation loop having a heater in thermal communication therewith; heating the first working fluid up to an operational temperature of above the boiling point of the first working fluid at one atmosphere; maintaining the first working fluid at the operational temperature of above the boiling point of the first working fluid for a period of time within the interior chamber; venting fluid unobstructedly and continuously from the chamber to outside of the chamber through a one-way one atmosphere check valve projecting through the inner wall of the chamber so as to maintain a pressure therein of approximately one atmosphere; continuously increasing the concentration of the first working fluid within the interior chamber to at least 85% concentration; maintaining the at least 85% concentration of the first working fluid for a duration of at least an order of 100 seconds; and exposing the item to be sterilized to the heated first working fluid in the interior chamber in a first mode of sterilization.

2. The method of claim 1, further comprising: introducing a second working fluid into the interior chamber holding the item to be sterilized; circulating the second working fluid in the interior chamber through the at least one fluid tight recirculation loop having a heater in thermal communication therewith for heating the second working fluid up to an operational temperature suitable for killing microorganisms; venting fluid unobstructedly and continuously from the chamber to outside of the chamber so as to maintain a pressure therein of approximately one atmosphere; continuously increasing the concentration of the second working fluid within the interior to a pre-set value; and exposing the item to be sterilized to the heated second working fluid in the interior chamber in a second mode of sterilization.

3. The method of claim 1, wherein the first mode of sterilization includes one of wet heat sterilization, dry heat sterilization, or chemical sterilization, wherein the chemical sterilization includes at least one of a liquid chemical or gaseous chemical.

4. The method of claim 2, wherein the second mode of sterilization includes another of wet heat sterilization, dry heat sterilization, or chemical sterilization, wherein the chemical sterilization includes at least one of a liquid chemical or gaseous chemical.

5. The method of claim 1 further comprising stirring the fluid introduced into the interior chamber within the chamber, wherein the stirring is performed by a means of circulation located within the chamber.

* * * * *